United States Patent
Keil et al.

(10) Patent No.: US 8,530,413 B2
(45) Date of Patent: Sep. 10, 2013

(54) HETEROCYCLICALLY SUBSTITUTED METHOXYPHENYL DERIVATIVES WITH AN OXO GROUP, PROCESSES FOR PREPARATION THEREOF AND USE THEREOF AS MEDICAMENTS

(75) Inventors: Stefanie Keil, Frankfurt am Main (DE); Elisabeth Defossa, Frankfurt am Main (DE); Viktoria Dietrich, Frankfurt am Main (DE); Siegfried Stengelin, Frankfurt am Main (DE); Andreas Herling, Frankfurt am Main (DE); Guido Haschke, Frankfurt am Main (DE); Thomas Klabunde, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/154,946

(22) Filed: Jun. 7, 2011

(65) Prior Publication Data
US 2012/0004165 A1 Jan. 5, 2012

Related U.S. Application Data

(60) Provisional application No. 61/422,788, filed on Dec. 14, 2010.

(30) Foreign Application Priority Data

Jun. 21, 2010 (EP) .................................... 10305662

(51) Int. Cl.
A61K 38/28 (2006.01)
A61P 5/50 (2006.01)

(52) U.S. Cl.
USPC ........................................... 514/6.5; 514/6.9

(58) Field of Classification Search
None
See application file for complete search history.

(56) References Cited

FOREIGN PATENT DOCUMENTS

| EP | 1559422 A1 | 8/2005 |
| EP | 2096109 A1 | 9/2009 |
| WO | WO 2005/086661 | * 9/2005 |
| WO | WO2005/086661 A2 | 9/2005 |
| WO | WO2007/033002 A1 | 3/2007 |

OTHER PUBLICATIONS

Itoh et al, Free fatty acids regulate insulin secretion from pancreatic beta cells through GPR40, Nature. Mar. 13, 2003;422(6928):173-6. Epub Feb. 23, 2003.*
Itoh et al, Free fatty acids regulate insulin secretion from pancreatic β cells through GPR40, Nature, 2003, 13:422, 173-176.*
Itoh, Yasuaki et al., "Free fatty acids regulate insulin secretion from pancreatic Beta cells through GPR40," Nature (2003), vol. 422, pp. 173-176.
European Search Report dated Sep. 29, 2010 issued in EP10305662.
International Search Report dated Jul. 27, 2011 issued in PCT/EP2011/060177.

* cited by examiner

*Primary Examiner* — Cecilia J Tsang
*Assistant Examiner* — Sergio Coffa

(57) ABSTRACT

Heterocyclically substituted methoxyphenyl derivatives with an oxo group, processes for preparation thereof and use thereof as medicaments
The invention relates to heterocyclically substituted methoxyphenyl derivatives with an oxo group, and to physiologically compatible salts thereof.
The invention relates to compounds of the formula I

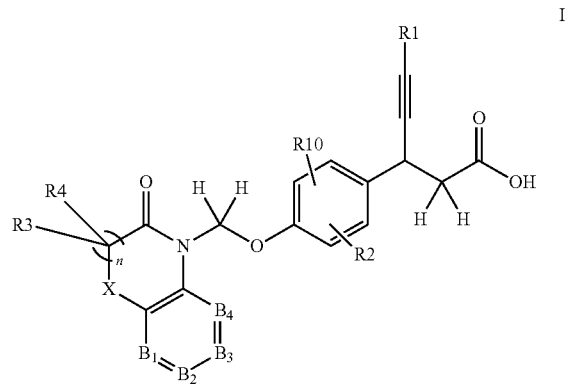

in which R1, R2, R3, R4, R10, X, n, $B_1$, $B_2$, $B_3$ and $B_4$ are each defined as specified, and to the physiologically compatible salts thereof. The compounds are suitable, for example, for treatment of diabetes.

12 Claims, No Drawings

HETEROCYCLICALLY SUBSTITUTED METHOXYPHENYL DERIVATIVES WITH AN OXO GROUP, PROCESSES FOR PREPARATION THEREOF AND USE THEREOF AS MEDICAMENTS

CROSS-REFERENCE TO RELATED APPLICATIONS

This application claims the benefit of U.S. Provisional Application No. 61/422,788 filed on Dec. 14, 2010.

Heterocyclically substituted methoxyphenyl derivatives with an oxo group, processes for preparation thereof and use thereof as medicaments The invention relates to heterocyclically substituted methoxyphenyl derivatives with an oxo group, and to physiologically compatible salts thereof.

It was an object of the invention to provide compounds which display a therapeutically utilizable action. It was a further object to find novel compounds suitable for treatment of hyperglycemia and of diabetes. It was a further object to find novel compounds which activate the GPR40 receptor and are thus suitable for treatment of hyperglycemia and of diabetes.

The invention therefore relates to compounds of the formula I in which

R1 is H, $(C_1-C_6)$-alkyl, $(C_3-C_6)$-cycloalkyl, $(C_1-C_6)$-alkylene-$(C_3-C_{10})$-cycloalkyl, where the alkyl radical, alkylene radical and cycloalkyl radical may be mono- or polysubstituted by fluorine;

R2, R10 are each independently H, F, Cl, Br, CN, $(C_1-C_6)$-alkyl, O—$(C_1-C_6)$-alkyl, where the alkyl radical may be mono- or polysubstituted by fluorine;

X is a bond, —O—, —SO—, —SO$_2$—, —CO—, —(CR7R8)-, —CH$_2$—CH$_2$—, —CH$_2$O—, —OCH$_2$—, —CH$_2$S—, —SCH$_2$—, —CH$_2$SO—, —SOCH$_2$—, —CH$_2$SO$_2$—, —SO$_2$CH$_2$—, —N(R11)-;

B$_1$, B$_2$, B$_3$, B$_4$ are each independently —N— or —C(R9)-;

R3, R4, R7, R8 are each independently H, $(C_1-C_6)$-alkyl, $(C_3-C_{10})$-cycloalkyl, $(C_1-C_6)$-alkylene-$(C_3-C_{10})$-cycloalkyl, where the alkyl radical, alkylene radical and cycloalkyl radical may be mono- or polysubstituted by fluorine;

R9 is H, F, Cl, Br, I, OH, NO$_2$, CN, O—$(C_1-C_6)$-alkyl, $(C_1-C_6)$-alkyl, SO$_2$—CH$_3$, SO$_2$—NH$_2$, SO$_2$—NH$(C_1-C_6)$-alkyl, SO$_2$—N$((C_1-C_6)$-alkyl$)_2$, CONH$_2$, CONH$(C_1-C_6)$-alkyl, CON$((C_1-C_6)$-alkyl$)_2$, SF$_5$, $(C_6-C_{10})$-aryl, $(C_3-C_{10})$-cycloalkyl, 4- to 12-membered heterocycle, where the $(C_1-C_6)$-alkyl radical, $(C_6-C_{10})$-aryl radical, $(C_3-C_{10})$-cycloalkyl radical, 4- to 12-membered heterocycle radical may be mono- or polysubstituted by F, Cl, Br, I, OH, CF$_3$, O—$(C_1-C_6)$-alkyl, $(C_1-C_6)$-alkyl, SF$_5$;

R11 is H, $(C_1-C_6)$-alkyl, —CO—$(C_1-C_6)$-alkyl;

n is 0, 1, 2;

and physiologically compatible salts thereof.

A further embodiment relates to compounds of the formula I in which one or more radicals have the following definitions:

R1 is H, $(C_1-C_6)$-alkyl, $(C_3-C_6)$-cycloalkyl, $(C_1-C_6)$-alkylene-$(C_3-C_{10})$-cycloalkyl, where the alkyl radical, alkylene radical and cycloalkyl radical may be mono- or polysubstituted by fluorine;

R2, R10 are each independently H, F, Cl, Br, CN, $(C_1-C_6)$-alkyl, O—$(C_1-C_6)$-alkyl, where the alkyl radical may be mono- or polysubstituted by fluorine;

X is a bond, —O—, —(CR7R8)-;

B$_1$, B$_2$, B$_3$, B$_4$ are each independently —N— or —C(R9)-;

R3, R4, R7, R8 are each independently H, $(C_1-C_6)$-alkyl, $(C_3-C_{10})$-cycloalkyl, $(C_1-C_6)$-alkylene-$(C_3-C_{10})$-cycloalkyl, where the alkyl radical, alkylene radical and cycloalkyl radical may be mono- or polysubstituted by fluorine;

R9 is H, F, Cl, Br, I, OH, NO$_2$, CN, O—$(C_1-C_6)$-alkyl, $(C_1-C_6)$-alkyl, SO$_2$—CH$_3$, SO$_2$—NH$_2$, SO$_2$—NH$(C_1-C_6)$-alkyl, SO$_2$—N$((C_1-C_6)$-alkyl$)_2$, CONH$_2$, CONH$(C_1-C_6)$-alkyl, CON$((C_1-C_6)$-alkyl$)_2$, SF$_5$, $(C_6-C_{10})$-aryl, $(C_3-C_{10})$-cycloalkyl, 4- to 12-membered heterocycle, where the $(C_1-C_6)$-alkyl radical, $(C_6-C_{10})$-aryl radical, $(C_3-C_{10})$-cycloalkyl radical, 4- to 12-membered heterocycle radical may be mono- or polysubstituted by F, Cl, Br, I, OH, CF$_3$, O—$(C_1-C_6)$-alkyl, $(C_1-C_6)$-alkyl, SF$_5$;

n is 0, 1;

and physiologically compatible salts thereof.

A further embodiment relates to compounds of the formula I in which one or more radicals have the following definitions:

R1 is $(C_1-C_6)$-alkyl, where the alkyl radical may be mono- or polysubstituted by fluorine;

R2 is H, F, Cl, Br, CN, $(C_1-C_6)$-alkyl, O—$(C_1-C_6)$-alkyl, where the alkyl radical may be mono- or polysubstituted by fluorine;

R10 is H;

X is a bond, —O—, —(CR7R8)-;

B$_1$, B$_2$, B$_3$, B$_4$ are each independently —N— or —C(R9)-;

R3, R4 are each independently H, $(C_1-C_6)$-alkyl;

R7, R8 are each independently H, $(C_1-C_6)$-alkyl;

R9 is F, Cl, Br, OH, $(C_1-C_6)$-alkyl, where the $(C_1-C_6)$-alkyl radical may be mono- to trisubstituted by F;

n is 0, 1;

and physiologically compatible salts thereof.

A further embodiment relates to compounds of the formula I in which one or more radicals have the following definitions:

R1 is $(C_1-C_6)$-alkyl, where the alkyl radical may be mono- or polysubstituted by fluorine;

R2 is H, F, Cl, Br, CN, $(C_1-C_6)$-alkyl, O—$(C_1-C_6)$-alkyl, where the alkyl radical may be mono- or polysubstituted by fluorine;

R10 is H;

X is a bond, —O—, —S—, —(CR7R8)-;

B$_1$, B$_2$, B$_3$, B$_4$ are each independently —N— or —C(R9)-;

R3, R4 are each independently H, $(C_1-C_6)$-alkyl;

R7, R8 are each independently H, $(C_1-C_6)$-alkyl;

R9 is H, F, Cl, Br, OH, $(C_1-C_6)$-alkyl, where the $(C_1-C_6)$-alkyl radical may be mono- to trisubstituted by F;

n is 0, 1;

and physiologically compatible salts thereof.

A further embodiment relates to compounds of the formula I in which one or more radicals have the following definitions:
R1 is CH$_3$;
R2 is H;
R10 is H;
X is a bond;
B$_1$, B$_2$, B$_3$, B$_4$ are each independently —N— or —C(R9);
R3, R4 are each independently H, (C$_1$-C$_6$)-alkyl;
R7, R8 are each independently H, (C$_1$-C$_6$)-alkyl;
R9 is H, F, Cl, Br, CF$_3$
n is 0, 1;
and physiologically compatible salts thereof.

A further embodiment relates to compounds of the formula I in which one or more radicals have the following definitions:
R1 is CH$_3$;
R2 is H;
R10 is H;
X is —O—;
B$_1$, B$_2$, B$_3$, B$_4$ are each independently —N— or —C(R9),
R3, R4 are each independently H, (C$_1$-C$_6$)-alkyl;
R7, R8 are each independently H, (C$_1$-C$_6$)-alkyl;
R9 is H, F, Cl, Br, CF$_3$;
n is 0, 1;
and physiologically compatible salts thereof.

A further embodiment relates to compounds of the formula I in which one or more radicals have the following definitions:
R1 is CH$_3$;
R2 is H;
R10 is H;
X is —S—;
B$_1$, B$_2$, B$_3$, B$_4$ are each independently —N— or —C(R9),
R3, R4 are each independently H, (C$_1$-C$_6$)-alkyl;
R7, R8 are each independently H, (C$_1$-C$_6$)-alkyl;
R9 is H, F, Cl, Br, CF$_3$;
n is 0, 1;
and physiologically compatible salts thereof. A further embodiment relates to compounds of the formula I in which one or more radicals have the following definitions:
R1 is CH$_3$;
R2 is H;
R10 is H;
X is —(CR7R8)-;
B$_1$, B$_2$, B$_3$, B$_4$ are each independently —N— or —C(R9),
R3, R4 are each independently H, (C$_1$-C$_6$)-alkyl;
R7, R8 are each independently H, (C$_1$-C$_6$)-alkyl;
R9 is H, F, Cl, Br, CF$_3$;
n is 0, 1;
and physiologically compatible salts thereof.

If radicals or substituents can occur more than once in the compounds of the formula I, they may each independently be defined as specified and be the same or different.

The alkyl radicals in the R1, R2, R3, R4, R7, R8, R9, R10 and R11 radicals may be either straight-chain or branched.

The invention relates to compounds of the formula I in the form of the salts, racemates, racemic mixtures and pure enantiomers thereof, and of the diastereomers and mixtures thereof.

The invention further provides both stereoisomer mixtures of the formula I and the pure stereoisomers of the formula I, and also diastereomer mixtures of the formula I and the pure diastereomers. The mixtures are separated, for example, by a chromatographic route.

The present invention encompasses all possible tautomeric forms of the compounds of the formula I.

Owing to their higher water solubility compared to the starting or base compounds, pharmaceutically acceptable salts are particularly suitable for medical applications. These salts must have a pharmaceutically acceptable anion or cation.

Salts with a pharmaceutically unacceptable anion likewise form part of the scope of the invention as useful intermediates for the preparation or purification of pharmaceutically acceptable salts and/or for use in nontherapeutic, for example in vitro, applications.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and the salts and solvates thereof, as described herein.

The compounds of the formula I possess the following structures where n is 0, 1 or

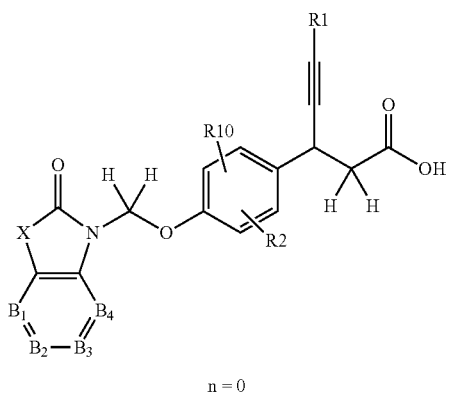

n = 0

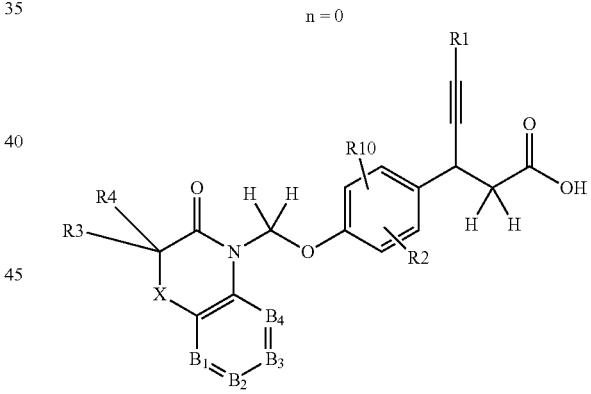

n = 1

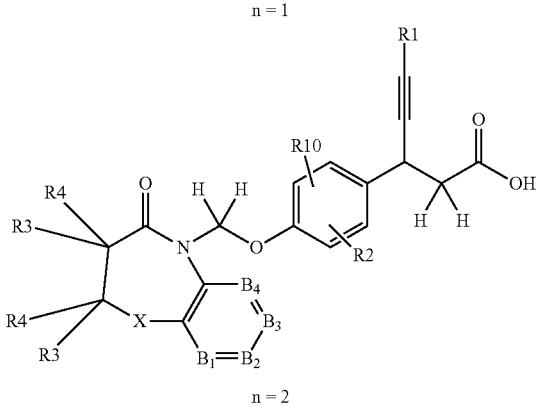

n = 2

An alkyl radical is understood to mean a straight-chain or branched hydrocarbon chain, for example methyl, ethyl, isopropyl, tert-butyl, hexyl. The alkyl radicals may be mono- or polysubstituted as described above.

An aryl radical is understood to mean a phenyl, naphthyl, biphenyl, tetrahydronaphthyl, alpha- or beta-tetralonyl, indanyl or indan-1-onyl radical.

The aryl radicals may be mono- or polysubstituted by suitable groups as described above.

"Heterocycle" and "heterocyclic radical" are understood to mean rings and ring systems which, apart from carbon, also contain heteroatoms, for example nitrogen, oxygen or sulfur. In addition, this definition also includes ring systems in which the heterocycle or the heterocyclic radical is fused to a further ring system. The heterocycle or the heterocyclic radical may be saturated, partly saturated or aromatic.

Suitable "heterocycles" or "heterocyclic radicals" are acridinyl, azepanyl, azocinyl, benzimidazolyl, benzofuryl, benzothienyl, benzothiophenyl, benzoxazolyi, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H, 6H-dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzooxazol-2-yl, 4,5,6,7-tetrahydro-berizothiazol-2-yl, 4,5,6,7-tetrahydrobenzoimidazol-2-yl, 4,5,6,7-tetrahydro-pyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl, tropanyl and xanthenyl.

The heterocycles or heterocyclic radicals may be mono- or polysubstituted by suitable groups as described above.

The invention also encompasses solvates, hydrates and alcohol adducts of the compounds of the formula I.

The compound(s) of the formula I may also be administered in combination with further active ingredients.

The amount of a compound of the formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid earlier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping resulting mixture.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Further suitable active ingredients for the combination preparations are:

All antidiabetics mentioned in the Rote Liste 2010, chapter 12; all weight-reducing agents/appetite suppressants mentioned in the Rote Liste 2010, chapter 1; all diuretics mentioned in the Rote Liste 2010, chapter 36; all lipid-lowering agents mentioned in the Rote Liste 2010, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), insulin degludec, insulin aspart, polyethylene glycosidized (PEGylated) Lispro as described in WO2009152128, Humulin®, VIAject™, SuliXen®, VIAject™ or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-lyn™ (Generex Biotechnology), or Technosphere® insulin (MannKind) or Cobalamin™ oral insulin or ORMD-0801 or insulins or insulin precursors as described in WO2007128815, WO2007128817, WO2008034881, WO2008049711, WO2008145721, WO2009034117, WO2009060071, WO2009133099 or insulins which can be administered transdermally; additionally included are also those insulin derivatives which are bonded to albumin by a bifunctional linker, as described, for example, in WO2009121884;

GLP-1 derivatives and GLP-1 agonists, for example exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037811, WO2006037810 by Novo Nordisk A/S, in WO 01/04156 by Zealand or in WO 00/34331 by Beaufour-Ipsen, pramlintide acetate (Symlin; Amylin Pharmaceuticals), inhalable GLP-1 (MKC-253 from MannKind) AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, WO2008148839, US2008299096, WO2008152403, WO2009030738, WO2009030771, WO2009030774, WO2009035540, WO2009058734, WO2009111700, WO2009125424, WO2009129696, WO2009149148, peptides, for example obinepitide (TM-30338), orally active GLP-1 analogs (e.g. NN9924 from Novo Nordisk), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, WO2009155257, WO2009155258, glycosylated GLP-1 derivatives as described in WO2009153960, and orally active hypoglycemic ingredients.

Antidiabetics also include gastrin analogs, for example TT-223.

Antidiabetics additionally include poly- or monoclonal antibodies directed, for example, against interleukin 1 beta (IL-1β), for example XOMA-052.

Antidiabetics additionally include peptides which can bind to the human pro-islet peptide (HIP) receptor, as described, for example, in WO2009049222.

Antidiabetics also include agonists of the glucose-dependent insulinotropic polypeptide (GIP) receptor, as described, for example, in WO2006121860.

Antidiabetics also include the glucose-dependent insulinotropic polypeptide (GIP), and also analogous compounds, as described, for example, in WO2008021560, WO2010016935, WO2010016936, WO2010016938, WO2010016940, WO2010016944.

Additionally included are analogs and derivatives of human pancreatic polypeptide, as described, for example, in WO2009007714.

Antidiabetics additionally include encapsulated insulin-producing porcine cells, for example DiabeCell®.

Antidiabetics also include analogs and derivatives of fibroblast growth factor 21 (FGF-21), as described, for example, in WO2009149171, WO2010006214.

The orally active hypoglycemic ingredients preferably include sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine fructose-6-phosphate amidotransferase (GFAT),
GLP-1 agonists,
potassium channel openers, for example pinacidil, cromakalim, diazoxide, diazoxide choline salt, or those as described in R. D. Carr et al., Diabetes 52, 2003, 2513.2518, in J. B. Hansen et al., Current Medicinal Chemistry 11, 2004, 1595-1615, in T. M. Tagmose et al., J. Med, Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S, active ingredients which act on the ATP-dependent potassium channel of the beta cells, inhibitors of dipeptidyl peptidase-IV (DPP-IV),
insulin sensitizers,
inhibitors of liver enzymes involved in stimulating gluconeogenesis and/or glycogenolysis,
modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC1 and/or ACC2) or
inhibitors of GSK-3 beta.

Also included are compounds which modify the lipid metabolism, such as active antihyperlipidemic ingredients and active antilipidemic ingredients,
HMG-CoA reductase inhibitors,
farnesoid X receptor (FXR) modulators,
fibrates,
cholesterol reabsorption inhibitors,
CETP inhibitors,
bile acid absorption inhibitors,
MTP inhibitors,
estrogen receptor gamma agonists (ERR γ agonists),
sigma-1 receptor antagonists,
antagonists of the somatostatin 5 receptor (SSTS receptor);
compounds which reduce food intake, and
compounds which increase thermogenesis.

In one embodiment of the invention, the compound of the formula I is administered in combination with insulin.

In another embodiment of the invention, the compound of the formula I is administered in combination with an insulin sensitizer, for example PN-2034 or ISIS-113715.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride, or those formulations as described, for example, in EP2103302.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin or one of its salts.

In a further embodiment, the compound of the formula I is administered in combination with a guanidine, for example benzylguanidine or one of its salts, or those guanidines as described in WO2009087395.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]phenyl]methyl]-2,4-thiazolidinedione. In one embodiment of the invention, the compound of the formula is administered in combination with a PPAR gamma agonist, for example rosiglitazone, pioglitazone, JTT-501, G1 262570, R-483, CS-011 (rivoglitazone), DRL-17564, DRF-2593 (balaglitazone), INT-131, T-2384, or those as described in WO2005086904, WO2007060992, WO2007100027, WO2007103252, WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008110062, WO2008126731, WO2008126732, WO2008137105, WO2009005672, WO2009038681, WO2009046606, WO2009080821, WO2009083526, WO2009102226, WO2009128558, WO2009139340.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982, JP2009023975, WO2009033561, WO2009047240, WO2009072581, WO2009080248, WO2009080242, WO2009149819, WO2009149820, WO2009147121, WO2009153496, WO2010008299, WO2010014771.

In one embodiment of the invention, the compound of the formula I is administered in combination with a mixed PPAR alpha/gamma agonist, for example naveglitazar, aleglitazar, LY-510929, ONO-5129, E-3030, AVE 8042, AVE 8134, AVE 0847, CKD-501 (lobeglitazone sulfate), MBX-213, KY-201, BMS-759509, or as described in WO 00/64888, WO 00/64876, WO03/020269, WO2004024726, WO2007099553, US2007276041, WO2007085135, WO2007085136, WO2007141423, WO2008016175, WO2008053331, WO2008109697, WO2008109700, WO2008108735, WO2009026657, WO2009026658, WO2009149819, WO2009149820 or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861, WO2009012650, US2009137671, WO2009080223, WO2009149819, WO2009149820, WO2010000353.

In one embodiment of the invention, the compound of the formula I is administered in combination with a pan-SP-PARM (selective PPAR modulator alpha, gamma, delta), for example GFT-505, indeglitazar, or those as described in WO2008035359, WO2009072581.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017, US2009076129.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760, WO2009016118, WO2009016119, WO2009030715, WO2009045830, WO2009045831, WO2009127723.

In another embodiment, the compound of the formula I is administered in combination with an inhibitor of the interaction of liver glycogen phosphorylase with the protein PPP1R3 subunit of glycogen-associated protein phosphatase 1 (PP1)), as described, for example, in WO2009030715.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244, WO2009057784, WO2009058662, WO2009058734, WO2009110520, WO2009120530, WO2009140342, WO2010019828.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754, US2008280875, WO2008136428, WO2008136444, WO2008149382, WO2008154563, WO2008156174, WO2008156757, US2009030046, WO2009018065, WO2009023718, WO2009039944, WO2009042435, WO2009046784, WO2009046802, WO2009047798, WO2009063821, WO2009081782, WO2009082152, WO2009083553, WO2009091014, US2009181981, WO2009092432, WO2009099080, WO2009106203, WO2009106209, WO2009109270, WO2009125873, WO2009127544, WO2009127546, WO2009128481, WO2009133687, WO2009140624, WO2010013161, WO2010015849, WO2010018800.

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628, WO2009012039, EP2058308, WO2009068467, WO2009068468.

In one embodiment, the compound of the formula I is administered in combination with modulators of glucose transporter 4 (GLUT4), for example KST-48 (D.-O. Lee et al.: Arzneim.-Forsch, Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, DSP-7238, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532, WO2010000469, WO2010015664.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a combination of a DPP-IV inhibitor with metformin hydrochloride, as described, for example, in WO2009121945.

In one embodiment, the compound of the formula I is administered in combination with a combination of a DPP-IV inhibitor with a GPR-119 agonist, as described, for example, in WO2009123992.

In one embodiment, the compound of the formula I is administered in combination with a combination of a DPP-IV inhibitor with miglitol, as described, for example, in WO2009139362.

In one embodiment, the compound of the formula I is administered in combination with a solid combination of a salt of sitagliptin with metformin hydrochloride.

In one embodiment, the compound of the formula I is administered in combination with a solid combination of alopliptin benzoate with pioglitazone hydrochloride.

In one embodiment, the compound of the formula I is administered in combination with a substance which enhances insulin secretion, for example KCP-265 (WO2003097064), or those as described in WO2007026761, WO2008045484, US2008194617, WO2009109259, WO2009109341.

In one embodiment, the compound of the formula I is administered in combination with agonists of the glucose-dependent insulinotropic receptor (GDIR), for example APD-668. In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 and/or 2 (SGLT1, SGLT2), for example KGA-2727, T-1095, SGL-0010, AVE 2268, SAR 7226, SGL-5083, SGL-5085, SGL-5094, ISIS-388626, sergliflozin, dapagliflozin or remogliflozin etabonate, canagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, US2008287529, WO2009026537, WO2009049731, WO2009076550, WO2009084531, WO2009096503, WO2009100936, WO2009121939, WO2009124638, WO2009128421, WO2009135673, WO2010009197, WO2010018435, WO2010018438 or by A. L. Handlon in Expert Opin. Ther. Patents (2005) 15(11), 1531-1540.

In a further embodiment of the invention, the compound of the formula I is administered in combination with a solid combination of an SGLT inhibitor with a DPP-IV inhibitor, as described in WO2009091082.

In one embodiment, the compound of the formula I is administered in combination with a stimulator of glucose transport, as described, for example, in WO2008136392, WO2008136393.

In one embodiment, the compound of the formula I is administered in combination with inhibitors of 11-beta-hydroxysteroid dehydrogenase 1 (11β-HSD1), for example BVT-2733, JNJ-25918646, INCB-13739, INCB-20817, D10-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834, WO2007145835, WO2007146761, WO2008000950, WO2008000951, WO2008003611, WO2008005910, WO2008006702, WO2008006703, WO2008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924, WO2008130951, WO2008134221, WO2008142859, WO2008142986, WO2008157752, WO2009001817, WO2009010416, WO2009017664, WO2009020140, WO2009023180, WO2009023181, WO2009023664, WO2009026422, WO2009038064, WO2009045753, WO2009056881, WO2009059666, WO2009061498, WO2009063061, WO2009070497, WO2009074789, WO2009075835, WO2009088997, WO2009090239, WO2009094169, WO2009098501, WO2009100872, WO2009102428, WO2009102460, WO2009102761, WO2009106817, WO2009108332, WO2009112691, WO2009112845, WO2009114173, WO2009117109, US2009264401, WO2009118473, WO2009131669, WO2009132986, WO2009134384, WO2009134387, WO2009134392, WO2009134400, WO2009135581, WO2009138386, WO2010006940, WO2010010157, WO2010010174, WO2010011917.

In one embodiment, the compound of the formula I is administered in combination with inhibitors of protein tyrosine phosphatase-1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058, US2008004325, WO2008033455, WO2008033931, WO2008033932, WO2008033934, WO2008089581, WO2008148744, WO2009032321, WO2009109999, WO2009109998.

In a further embodiment, the compound of the formula I is administered in combination with stimulators of tyrosine kinase B (Trk-B), as described, for example, in WO2010014613.

In a further embodiment, the compound of the formula I is administered in combination with beta 3 agonists (also called beta-3 adrenoceptor agonists), as described, for example, in Physiol. Behav. 2004 Sep. 15; 82(2-3):489-96, J Clin Invest (1998) 101: 2387-93, Curr. Pharma. Des. 2001 September; 7(14):1433-49., Bioorganic & Medicinal Chemistry Letters volume 14, number 13, Jul. 5, 2004, pages 3525-3529 (BMS-201620).

In one embodiment of the invention, the compound of the formula I is administered in combination with an agonist of GPR109A (HM74A receptor agonists; NAR agonists (nicotinic acid receptor agonists)), for example nicotinic acid or extended release niacin in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007002557, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered combination with a solid combination of niacin with simvastatin.

In another embodiment of the invention, the compound of the formula I is administered in combination with nicotinic acid or "extended release niacin" in conjunction with MK-0524A (laropiprant).

In a further embodiment of the invention, the compound of the formula I is administered in combination with nicotinic acid or "extended release niacin" in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with a solid combination of niacin with meloxicam, as described, for example, in WO2009149056.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056, WO2010012650.

In one embodiment, the compound of the formula I is administered in combination with modulators of GPR119 (G-protein-coupled glucose-dependent insulinotropic receptor), for example PSN-119-1, PSN-821, PSN-119-2, MBX-2982 or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702, WO2008130581, WO2008130584, WO2008130615, WO2008137435, WO2008137436, WO2009012275, WO2009012277, WO2009014910, WO2009034388, WO2009038974, WO2009050522, WO2009050523, WO2009055331, WO2009105715, WO2009105717, WO2009105722, WO2009106561, WO2009106565, WO2009117421, WO2009125434, WO2009126535, WO2009129036, US2009286812, WO2009143049, WO2009150144, WO2010001166, WO2010004343, WO2010004344, WO2010004345, WO2010004346, WO2010004347, WO2010004348, WO2010008739, WO2010006191, WO2010009183, WO2010009195, WO2010009207, WO2010009208, WO2010014593.

In a further embodiment, the compound of the formula I is administered in combination with modulators of GPR120, as described, for example, in EP1688138, WO2008066131, WO2008066131, WO2008103500, WO2008103501, WO2008139879, WO2009038204, WO2009147990, WO2010008831.

In another embodiment, the compound of the formula I is administered in combination with antagonists of GPR105, as described, for example, in WO2009000087, WO2009070873.

In a further embodiment, the compound of the formula I is administered in combination with agonists of GPR43, for example ESN-282.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837, WO2008122352, WO2008122357, WO2009009287.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002, or those as described in WO2008048866, WO20080488867, US2009062369.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064, EP-1992620, EP-1992621, EP1992624, EP-1992625, WO2008130312, WO2009007029, EP2020232, WO2009017452, WO2009035634, WO2009035684, WO2009038385, WO2009095787, WO2009095788, WO2009095789, WO2009095792, WO2009145814, US2009291982, WO2009154697, WO2009156857, WO2009156859, WO2009156860, WO2009156861, WO2009156863, WO2009156864, WO2009156865, WO2010013168, WO2010014794.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of phosphoinositide kinase-3 (PI3K), for example those as described in WO2008027584, WO2008070150, WO2008125833, WO2008125835, WO2008125839, WO2009010530, WO2009026345, WO2009071888, WO2009071890, WO2009071895.

In one embodiment, the compound of the formula I is administered in combination with an inhibitor of serum/glucocorticoid-regulated kinase (SGK), as described, for example, in WO2006072354, WO2007093264, WO2008009335, WO2008086854, WO2008138448.

In one embodiment, the compound of the formula I is administered in combination with a modulator of the glucocorticoid receptor, as described, for example, in WO2008057855, WO2008057856, WO2008057857, WO2008057859, WO2008057862, WO2008059867, WO2008059866, WO2008059865, WO2008070507, WO2008124665, WO2008124745, WO2008146871, WO2009015067, WO2009040288, WO2009069736, WO2009149139.

In one embodiment, the compound of the formula I is administered in combination with a modulator of the mineralocorticoid receptor (MR), for example drospirenone, or those as described in WO2008104306, WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator/modulator of the AMP-activated protein kinase (AMPK), as described, for example, in WO2007062568, WO2008006432, WO2008016278, WO2008016730, WO2008020607, WO2008083124, WO2008136642, WO2009019445, WO2009019446, WO2009019600, WO2009028891, WO2009065131, WO2009076631, WO2009079921, WO2009100130, WO2009124636, WO2009135580, WO2009152909.

In one embodiment, the compound of the formula I is administered in combination with an inhibitor of ceramide kinase, as described, for example, in WO2007112914, WO2007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "1-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075, WO2009056693, WO2009075277, WO2009089042, WO2009120801.

In another embodiment, the compound of the formula I is administered in combination with inhibitors of NF-kappaB (NFKB) activation, for example salsalate.

In a further embodiment, the compound of the formula I is administered in combination with inhibitors of ASK-1 (apoptosis signal-regulating kinase 1), as described, for example, in WO2008016131, WO2009123986.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, NCX-6560, or those as described in US2007249583, WO2008083551, WO2009054682.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222, JP2008273847, WO2008157270, US2008299118, US2008300235, WO2009005998, WO2009012125, WO2009027264, WO2009062874, US2009131409, US2009137554, US2009163552, WO2009127321, EP2128158.

In another embodiment of the invention, the compound of the formula I is administered in combination with a ligand of the liver X receptor (LXR), as described, for example, in WO2007092965, WO2008041003, WO2008049040, WO2008065754, WO2008073825, US2008242677, WO2009020683, US2009030082, WO2009021868, US2009069373, WO2009024550, WO2009040289, WO2009086123, WO2009086129, WO2009086130, WO2009086138, WO2009107387, US2009247587, WO2009133692, WO2008138438, WO2009144961, WO2009150109.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348; Trilipix™).

In one embodiment of the invention, the compound of the formula I is administered in combination with fibrates, for example the choline salt of fenofibrate (Trilipix™) and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia®, a solid combination of fenofibrate with metformin.

In another embodiment of the invention, the compound of the formula I is administered in combination with a solid combination of metformin with an MTP inhibitor, as described in WO2009090210.

In one embodiment of the invention, the compound of the formula I is administered in combination with a cholesterol reabsorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300, WO2008104875, US2008280836, WO2008108486.

In one embodiment of the invention, the compound of the formula I is administered in combination with an NPC1L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. No. 6,992,067 or U.S. Pat. No. 7,205,290.

In a further embodiment of the invention, the further active ingredient is a diphenylazetidinone derivative, as described, for example, in U.S. Pat. No. 6,992,067 or U.S. Pat. No. 7,205,290, combined with a statin, for example simvastatin, fluvastatin, pravastatin, lovastatin, cerivastatin, atorvastatin, pitavastatin or rosuvastatin.

In one embodiment of the invention, the compound of the formula I is administered in combination with a solid combination of lapaquistat, a squalene synthase inhibitor, with atorvastatin.

In a further embodiment of the invention, the compound of the formula I is administered in combination with a conjugate consisting of the HMG-CoA reductase inhibitor atorvastatin with the renin inhibitor aliskiren (WO2009090158).

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO2008059513, WO2008070496, WO2008115442, WO2008111604, WO2008129951, WO2008141077, US2009118287, WO2009062371, WO2009071509.

In one embodiment of the invention, the compound of the formula I is administered in combination with bile acid reabsorption inhibitors (inhibitors of the intestinal bile acid transporter (IBAT)) (see, for example, U.S. Pat. No. 6,245,744, U.S. Pat. No. 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1 (G-protein-coupled bile acid receptor 1; TGR5), for example INT-777 or those as described, for example, in US20060199795, WO2007110237, WO200'7127505, WO2008009407, WO2008067219, WO2008067222, FR2908310, WO2008091540, WO2008097976, US2009054304, WO2009026241, WO2009146772, WO2010014739, WO2010014836.

In one embodiment, the compound of the formula I is administered in combination with modulators of histone deacetylase, for example ursodeoxycholic acid, as described in WO2009011420.

In one embodiment, the compound of the formula I is administered in combination with inhibitors/modulators of the TRPM5 channel (TRP cation channel M5), as described, for example, in WO2008097504, WO2009038722.

In one embodiment, the compound of the formula I is administered in combination with inhibitors/modulators of the TRPA1 channel (TRP cation channel A1), as described, for example, in US2009176883, WO2009089083, WO2009144548.

In one embodiment, the compound of the formula I is administered in combination with inhibitors/modulators of the TRPV3 channel (TRP cation channel V3), as described, for example, in WO2009084034, WO2009130560.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with tocotrienol and insulin or an insulin derivative.

In one embodiment of the invention, the compound of the formula I is administered in combination with a chewing gum comprising phytosterols (Reductol™).

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, JTT-130, or those as described in WO2005085226, WO2005121091, WO2006010423, WO2006113910, WO2007143164, WO2008049806, WO2008049808, WO2008090198, WO2008100423, WO2009014674.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189, WO2009030746, WO2009030747, WO2009030750, WO2009030752, WO2009070130, WO2009081957, WO2009081957.

In a further embodiment of the invention, the compound of the formula I is administered in combination with an inhibitor of liver carnitine palmitoyltransferase-1 (L-CPT1), as described, for example, in WO2007063012, WO2007096251 (ST-3473), WO2008015081, US2008103182, WO2008074692, WO2008145596, WO2009019199, WO2009156479, WO2010008473.

In another embodiment of the invention, the compound of the formula I is administered in combination with an inhibitor of carnitin O-palmitoyltransferase II (CPT2), as described, for example, in US2009270500, US2009270505, WO2009132978, WO2009132979.

In a further embodiment of the invention, the compound of the formula I is administered in combination with a modulator of serine palmitoyltransferase (SPT), as described, for example, in WO2008031032, WO2008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO2005077907,

JP2007022943, WO2008003424, WO2008132846, WO2008133288, WO2009136396.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with apolipoprotein (ApoB) SNALP, a therapeutic product which comprises an siRNA (directed against the ApoB gene).

In one embodiment of the invention, the compound of the formula I is administered in combination with a stimulator of the ApoA-1 gene, as described, for example, in WO2008092231.

In one embodiment of the invention, the compound of the formula I is administered in combination with a modulator of the synthesis of apolipoprotein for example ISIS-APOCII-IRx.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278, WO2009071099, WO2009086096, US2009247550.

In one embodiment of the invention, the compound of the formula I is administered in combination with an ABCA1 expression enhancer, as described, for example, in WO2006072393, WO2008062830, WO2009100326.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), for example CVT-3619 or those as described, for example, in EP1258247, EP1375508, WO2008028590, WO2008077050, WO2009050199, WO2009080197, WO2009100827, WO2009112155.

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923, WO2008070661, WO2009010871.

In a further embodiment of the invention, the compound of the formula I is administered in combination with a ligand of the adenosine A1/A2B receptors, as described, for example, in WO2008064788, WO2008064789, WO2009080198, WO2009100827, WO2009143992.

In one embodiment of the invention, the compound of the formula I is administered in combination with an adenosine A2B receptor antagonist (adenosine A2B R), as described in US2007270433, WO2008027585, WO2008080461, WO2009037463, WO2009037467, WO2009037468, WO2009118759.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833, WO2008065508, WO2008069500, WO2008070609, WO2008072850, WO2008079610, WO2008088688, WO2008088689, WO2008088692, US2008171761, WO2008090944, JP2008179621, US2008200461, WO2008102749, WO2008103382, WO2008121592, WO2009082346, US2009253725, JP2009196966, WO2009144554, WO2009144555, WO2010003624, WO2010002010.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833) or with modulators of mitochondrial glycerol-3-phosphate O-acyltransferase, described in WO2010005922.

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO2008112022, WO2009011872, WO2009049154, WO2009049157, WO2009049165, WO2009073772, WO2009097476, WO2009111207, WO2009129508, WO2009151800.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A) or velneperit or those as described in WO2009110510;

NPY-5 receptor antagonists/receptor modulators, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891, WO2008129007, WO2008134228, WO2009054434, WO2009095377, WO2009131096;

NPY-4 receptor antagonists, as described, for example, in WO2007038942;

NPY-2 receptor antagonists/modulators, as described, for example, in WO2007038943, WO2009006185, US2009099199, US2009099243, US2009099244, WO2009079593, WO2009079597;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947, WO2009080608;

NPY-2 receptor agonists, as described, for example, in WO2009080608;
derivatives of the peptide obestatin, as described by WO2006096847;
CB1R (cannabinoid receptor 1) antagonists/inverse agonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO200508034, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO200405825, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136571, WO2007136607, WO2007136571, U.S. Pat. No. 7,297,710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, WO2998043544, WO2008044111, WO2008048648, EP1921072-A1, WO2008053341, WO2008056377, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO2008120000, WO2008121257, WO2008127585, WO2008129157, WO2008130616, WO2008134300, US2008262066, US2008287505, WO2009005645, WO2009005646, WO2009005671, WO2009023292, WO2009023653, WO2009024819, WO2009033125, EP2042175, WO2009053548-WO2009053553, WO2009054923, WO2009054929, WO2009059264, WO2009073138, WO2009074782, WO2009075691, WO2009078498, WO2009087285, WO2009074782, WO2009097590, WO2009097995, WO2009097996, WO2009097998, WO2009097999, WO2009098000, WO2009106708, US2009239909, WO2009118473, US2009264436, US2009264476, WO2009130234, WO2009131814, WO2009131815, US2009286758, WO2009141532, WO2009141533, WO2009153569, WO2010003760, WO2010012437, WO2010019762;
cannabinoid receptor 1/cannabinoid receptor 2 (CB1,/CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618, WO2009007697, WO2009012227, WO2009087564, WO2009093018, WO2009095752, WO2009120660, WO2010012964;
cannabinoid receptor 2 (CB2) modulating compounds, for example those as described, for example, in WO2008063625, WO2008157500, WO2009004171, WO2009032754, WO2009055357, WO2009061652, WO2009063495, WO2009067613, WO2009114566;
modulators of FAAH (fatty acid amide hydrolase), as described, for example, in WO2007140005, WO2008019357, WO2008021625, WO2008023720, WO2008030532, WO2008129129, WO2008145839, WO2008145843, WO2008147553, WO2008153752, WO2009011904, WO2009048101, WO2009084970, WO2009105220, WO2009109504, WO2009109743, WO2009117444, WO2009127944, WO2009138416, WO2009151991, WO2009152025, WO2009154785, WO2010005572, WO2010017079;
inhibitors of fatty acid synthase (FAS), as described, for example, in WO2008057585, WO2008059214, WO2008075064, WO2008075070, WO2008075077, WO2009079860;
inhibitors of LCE (long chain fatty acid elongase)/long chain fatty acid CoA ligase, as described, for example, in WO2008120653, WO2009038021, WO2009044788, WO2009081789, WO2009099086;
vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863, WO2008125295, WO2008125296, WO2008125337, WO2008125342, WO2008132600, WO2008133973, WO2009010529, WO2009010824, WO2009016241, WO2009023539, WO2009038812, WO2009050348, WO2009055629, WO2009055749, WO2009064449, WO2009081222, WO2009089057, WO2009109710WO2009112677, WO2009112678, WO2009112679, WO2009121036, WO2009124551, WO2009136625, WO2010002209;
modulators, ligands, antagonists or inverse agonists of the opioid receptors, for example GSK-982 or those as described, for example, in WO2007047397, WO2008021849, WO2008021851, WO2008032156, WO2008059335, WO2008125348, WO2008125349, WO2008142454, WO2009030962, WO2009103552, WO2009115257;
modulators of the "orphan opioid (ORL-1) receptor", as described, for example, in US2008249122, WO2008089201; agonists of the prostaglandin receptor, for example bimatoprost or those compounds as described in WO2007111806;
MC4 receptor agonists (melanocortin-4 receptor agonists, MC4R agonists, for example N-[2-(3a-benzyl-2-methyl-3-oxo-2,3,3a,4,6,7-hexahydropyrazolo[4,3-c]pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2004089307, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186-WO2008087190, WO2008090357, WO2008142319, WO2009015867, WO2009061411, US2009076029, US2009131465, WO2009071101, US2009305960, WO2009144432, WO2009151383, WO2010015972;
MC4 receptor modulators (melanocortin-4 receptor modulators), as described, for example, WO2009010299, WO2009074157;
orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5] naphthyridin-4-ylurea hydrochloride (SB-334867-A), or those as described, for example, in WO200196302, WO2008185693, WO2004085403, WO2005075458, WO2006067224, WO2007085718, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125, WO2008147518, WO2008150364, WO2009003993, WO2009003997, WO2009011775, WO2009016087, WO2009020642, WO2009058238, US2009186920, US2009203736, WO2009092642, WO2009100994, WO2009104155, WO2009124956, WO2009133522, WO2009156951, WO2010017260);
histamine H3 receptor antagonists/inverse agonists (e.g. 3-cyclohexyl-1-(4,4-dimethyl-1,4,6,7-tetrahydroimidazo[4, 5-c]pyridin-5-yl)propan-1-one oxalic acid salt (WO 00/63208), or those as described in WO200064884, WO2005082893, WO2005123716, US2005171181 (e.g. PF-00389027), WO2006107661, WO2007003804, WO2007016496, WO2007020213, WO2007049798, WO2007055418, WO2007057329, WO2007062999, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EP1757594, WO2008068173, WO2008068174, US20080 71753, WO2008072703, WO2008072724, US2008188484, US2008188486, US2008188487, WO2008109333, WO2008109336, WO2008126886, WO2008154126, WO2008151957, US2008318952, WO2009003003, WO2009013195, WO2009036132, WO2009039431, WO2009045313, WO2009058300, WO2009063953, WO2009067401, WO2009067405, WO2009067406, US2009163464, WO2009100120, WO2009105206, WO2009121812, WO2009126782, WO2010011653, WO2010011657);
histamine H1/histamine H3 modulators, for example betahistine or its dihydrochloride;
modulators of the histamine H3 transporter or of the histamine H3/serotonin transporter, as described, for example, in WO2008002816, WO2008002817, WO2008002818, WO2008002820;
modulators of vesicular monoamine transporter 2 (VMAT2), as described, for example, in WO2009126305;
histamine H4 modulators, as described, for example, in WO2007117399, US2009156613;
CRF antagonists (e.g. [2-methyl-9-(2,4,6-methylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070, WO2010015628, WO2010015655);
CRF BP antagonists (e.g. urocortin);
urocortin agonists;
modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103, WO2008132162;
MSH (melanocyte-stimulating hormone) agonists;
MCH (melanme-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO2008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409, US2008269110, WO2008140239, WO2009021740, US2009011994, US2009082359, WO2009041567, WO2009076387, WO2009089482, WO2009103478, WO2009119726, WO2009120655, WO2009123194, WO2009137270, WO2009146365, WO2009154132);

CCK-A (CCK-1) modulators (for example {2-[4-(4-chloro-2,5-dimethoxyphenyl)-5-(2-cyclohexylethyl)thiazol-2-yl-carbamoyl]-5,7-dimethylindol-1-yl}acetic acid trifluoroacetic acid salt (WO 99/15525) or SR-146131 (WO0244150) or SSR-125180) or those as described in WO2005116034, WO2007120655, WO2007120688, WO2007120718, WO2008091631;

serotonin reuptake inhibitors (e.g. dexfenfluramine), or those as described in WO2007148341, WO2008034142, WO2008081477, WO2008120761, WO2008141081, WO2008141082, WO2008145135, WO2008150848, WO2009043834, WO2009077858;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947 or those as described in WO2009016214, WO2009016215, WO2009077584, WO2009098208, WO2009098209, WO2009106769, WO2009109517, WO2009109518, WO2009109519, WO2009109608, WO2009145357, WO2009149258;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118, WO2008150480;

dopamine antagonists, as described, for example, in WO2008079838, WO2008079839, WO2008079847, WO2008079848;

norepinephrine reuptake inhibitors, as described, for example, in US2008076724, WO2009062318;

5-HT1A receptor modulators, as described, for example, in WO2009006227, WO2009137679, WO2009137732;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213, WO2008007661, WO2008007664, WO2008009125, WO2008010073, WO2008108445, WO2009063991, WO2009063992, WO2009063993, WO2009079765);

5-HT6 receptor modulators, for example E-6837, BVT-74316, PF-3246799 or PRX-07034, or those as described, for example, in WO2005058858, WO2007054257, WO2007107373, WO2007108569, WO2007108742-744, WO2008003703, WO2008027073, WO2008034815, WO2008054288, EP 1947085, WO2008084491, WO2008084492, WO2008092665, WO2008092666, WO2008101247, WO2008110598, WO2008116831, WO2008116833, WO2008117169, WO2008136017, WO2008147812, EP2036888, WO2009013010, WO2009034581, WO2009053997, WO2009056632, WO2009073118, WO2009115515, WO2009135925, WO2009135927, WO2010000456, WO2010012806, EP2145887;

agonists of estrogen receptor gamma ERRγ agonists), as described, for example, in WO2007131005, WO2008052709;

agonists of estrogen receptor alpha (ERRα/ERR1 agonists), as described, for example, in WO2008109727;

agonists of estrogen receptor beta (ERRβ agonists), as described, for example in WO2009055734, WO2009100335, WO2009127686;

sigma-1 receptor antagonists, as described, for example, in WO2007098953, WO2007098961, WO2008015266, WO2008055932, WO2008055933, WO2009071657; muscarin 3 receptor (M3R) antagonists, as described, for example, in WO2007110782, WO2008041184;

bombesin receptor agonists (BRS-3 agonists), as described, for example, in WO2008051404, WO2008051405, WO2008051406, WO2008073311;

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457, WO2008008286, WO2009056707;

growth hormone secretagogue receptor modulators (ghrelin modulators), for example JMV-2959, JMV-3002, JMV-2810, JMV-2951, or those as described in WO2006012577 (e.g. YIL-781 or YIL-870), WO2007079239, WO2008092681, WO2008145749, WO2008148853, WO2008148854, WO2008148856, WO2009047558, WO2009071283, WO2009115503;

TRH agonists for example, EP 0 462 884);

decoupling protein 2 or 3 modulators (as described, for example, in WO2009128583);

chemical decouplers (e.g. WO2008059023, WO2008059024, WO2008059025, WO2008059026);

leptin receptor agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

leptin receptor modulators, as described, for example, in WO2009019427, WO2009071658, WO2009071668, WO2009071677, WO2009071678, WO2009147211, WO2009147216, WO2009147219, WO2009147221;

DA agonists (bromocriptin, bromocriptin mesylate, doprexin) or those as described in US2009143390;

lipase/amylase inhibitors (e.g. WO 00/40569, WO2008107184, WO2009049428, WO2009125819);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221, WO2008129319, WO2008141976, WO2008148840, WO2008148849, WO2008148851, WO2008148868, WO2009011285, WO2009016462, WO2009024821, US2009076275, WO2009040410, WO2009071483, WO2009081195, WO2009119534, WO2009126624, WO2009126861, WO2010007046, WO2010017040;
inhibitors of monoacylglycerol acyltransferase (2-acylglycerol O-acyltransferase; MGAT), as described, for example, in WO2008038768;
inhibitors of fatty acid synthase (FAS), for example C75, or those as described in WO2004005277, WO2008006113;
inhibitors of stearoyl-CoA delta9 desaturase (SCD1), as described, for example, in WO2007009236, WO2007044085, WO2007046867, WO2007046868, WO20070501124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349, WO2008128335, WO2008135141, WO2008139845, WO2008141455, US20080255130, US2008255161, WO2008141455, WO2009010560, WO2009016216, WO2009012573, WO2009024287, JP2009019013, WO2009037542, WO2009056556, WO2009060053, WO2009060054, WO2009070533, WO2009073973, WO2009103739, WO2009117659, WO2009117676, US2009253693, US2009253738, WO2009124259, WO2009126123, WO2009126527, WO2009129625, WO2009137201, WO2009150196, WO2009156484, WO2010006962, WO2010007482;
inhibitors of fatty acid desaturase 1 (delta5 desaturase), as described, for example, in WO2008089310;
inhibitors of monoglyceride (MGL), as described in WO2008145842;
hypoglycemic/hypertriglyceridemic indoline compounds, as described in WO2008039087, WO2009051119;
inhibitors of "adipocyte fatty acid-binding protein aP2", for example BMS-309403 or those as described in WO2009028248;
activators of adiponectin secretion, as described, for example, in WO2006082978, WO2008105533, WO2008136173;
promoters of adiponectin production, as described, for example, in WO2007125946, WO2008038712;
modified adiponectins, as described, for example, in WO2008121009;
oxyntomodulin or analogs thereof (for example, TKS-1225);
oleoyl-estrone
or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213, JP2009155261;
or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (SIP), for example PF-429242.

In a further embodiment of the invention, the compound of the formula I is administered in combination with a modulator of the "trace amine associated receptor I" (TAAR1), as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaze™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, AGI-1067 (succinobucol), probucol, tocopherol, ascorbic acid, β-carotene or selenium, or those as described in WO2009135918.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In a further embodiment, the compound of the formula I is administered in combination with an activator of soluble guanylate cyclase (sGC), as described, for example, in WO2009032249.

In another embodiment, the compound of the formula I is administered in combination with an inhibitor of carboanhydrase type 2 (carbonic anhydrase type 2), for example those as described in WO2007065948, WO2009050252.

In another embodiment, the compound of the formula I is administered in combination with topiramat or a derivative thereof, as described in WO2008027557, US2009304789.

In a further embodiment, the compound of the formula I is administered in combination with a solid combination of topiramat with phentermin (Qnexa™).

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463, WO2009035159, WO2009035162.

In one embodiment, the compound of the formula I is administered in combination with a "c-Jun N-terminal kinase" inhibitor (JNK inhibitor), for example B1-78D3 or those as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with inhibitors of neutral endopeptidase (NEP inhibitors), as described, for example, in WO2009138122, WO2009135526.

In one embodiment, the compound of the formula I is administered in combination with modulators of the glucocorticoid receptor (GR), for example KB-3305 or those compounds as described, for example, in WO2005090336, WO2006071609, WO2006135826, WO2007105766, WO2008120661, WO2009040288, WO2009058944, WO2009108525, WO2009111214.

In one embodiment, the further active ingredient is varenicline tartrate, a partial agonist of the alpha 4-beta 2 nicotinic acetylcholine receptor.

In one embodiment, the further active ingredient is an agonist of the alpha 7-nicotinic acetylcholine receptor, as described, for example, in WO2009018551, WO2009071519, WO2009071576, WO2009071577.

In one embodiment, the further active ingredient is trodusquemine.

In one embodiment, the further active ingredient is a modulator of the enzyme SIRT1 and/or SIRT3 (an $NAD^+$-dependent protein deacetylase); this active ingredient may, for example, be resveratrol in suitable formulations, or those compounds as specified in WO2007019416 (e.g. SRT-1720), WO2008073451, WO2008156866, WO2008156869, WO2009026701, WO2009049018, WO2009058348, WO2009061453, WO2009134973, WO2009146358, WO2010003048.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2004000803, WO2006000804, WO2004000805, WO2004087655, WO2005113496, WO2007059871, WO2007107587, WO2007111994, WO2008052658, WO2008106600, WO2008113796, US2008280836, WO2009113952, US2009312302

In a further embodiment, the compound of the formula I is administered in combination with inhibitors of SREBP (sterol regulatory element-binding protein), for example fatostatin, or those as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin;
see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine, In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In another embodiment, the further active ingredient is a neuropeptide FF2 agonist, as described, for example, in WO2009038012.

In one embodiment, the further active ingredient is a nasal calcium channel blocker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936, WO2009107660.

In one embodiment, the further active ingredient is an inhibitor of the calcium metabolism, for example those as described in US2009124680.

In one embodiment, the further active ingredient is a blocker of the "T-type calcium channel", as described, for example, in WO2008033431, WO2008110008, US2008280900, WO2008141446, US2009270338, WO2009146540, US2009325979, WO2009146539.

In one embodiment, the further active ingredient is an inhibitor of KCNQ potassium channel 2 or 3, for example those as described in US2008027049, US2008027090.

In one embodiment, the further active ingredient is a modulator of KCNN potassium channel 1, 2 or 3 (modulators of the SK1, SK2 and/or SK3 channel), for example those as described in US2009036475.

In one embodiment, the further active ingredient is an inhibitor of the potassium Kv1.3 ion channel, for example those as described in WO2008040057, WO2008040058, WO2008046065, WO2009043117.

In one embodiment, the further active ingredient is a potassium channel modulator, for example those as described in WO2008135447, WO2008135448, WO2008135591, WO2009099820.

In a further embodiment, the further active ingredient is a hyperpolarization-activated cyclic nucleotide-gated (HCN) potassium-sodium channel inhibitor, for example those as described in US2009069296.

In another embodiment, the further active ingredient is an inhibitor of the sodium-potassium-2 chloride (NKCC1) cotransporter, for example those as described in WO2009130735.

In another embodiment, the further active ingredient is a voltage-gated sodium channel inhibitor, for example those as described in WO2009049180, WO2009049181.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 3 (SSTR3), for example those as described in WO2009011836.

In one embodiment, the further active ingredient is a modulator of somatostatin receptor 5 (SSTR5), for example those as described in WO2008019967, US2008064697, US2008249101, WO2008000692, US2008293756, WO2008148710.

In one embodiment, the further active ingredient is a modulator of somatostatin receptor 2 (SSTR2), for example those as described in WO2008051272.

In one embodiment, the further active ingredient is a compound which is capable of reducing the amount of retinol-binding protein 4 (RBP4), for example those as described in WO2009051244, WO2009145286.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO2008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin II receptor antagonist, for example those as described in WO2008062905, WO2008067378, WO2008062905.

In one embodiment, the further active ingredient is an agonist of the sphingosine 1-phosphate receptor (SIP), for example those as described in WO2008064315, WO2008074820, WO2008074821, WO2008135522, WO2009019167, WO2009043013, WO2009080663, WO2009085847, WO2009151529, WO2009151621, WO2009151626, WO2009154737.

In one embodiment, the further active ingredient is an agent which retards gastric emptying, for example 4-hydroxyisoleucine (WO2008044770).

In one embodiment, the further active ingredient is a trytophan-5-hydroxylase inhibitor-1 (TPH1 inhibitor), which modulates gastrointestinal motility, as described, for example, in WO2009014972.

In one embodiment, the further active ingredient is a muscle-relaxing substance, as described, for example, in WO2008090200.

In a further embodiment, the further active ingredient is an inhibitor of monoamine oxidase B (MAO-B), for example those as described in WO2008092091, WO2009066152.

In a further embodiment, the further active ingredient is an inhibitor of monoamine oxidase A (MAO-A), for example those as described in WO2009030968.

In another embodiment, the further active ingredient is an inhibitor of the binding of cholesterol and/or triglycerides to the SCP-2 protein (sterol carrier protein-2), for example those as described in US2008194658.

In a further embodiment, the further active ingredient is a compound which binds to the β-subunit of the trimeric GTP-binding protein, for example those as described in WO2008126920.

In one embodiment, the further active ingredient is a urate anion exchanger inhibitor 1, as described, for example, in WO2009070740.

In one embodiment, the further active ingredient is a modulator of the ATP transporter, as described, for example, in WO2009108657.

In another embodiment, the further active ingredient is lisofylline, which prevents autoimmune damage to insulin-producing cells.

In yet another embodiment, the further active ingredient is an extract from *Bidens pilosa* with the ingredient cytopiloyne as described in EP 1955701.

In one embodiment, the further active ingredient is an inhibitor of glucosylceramide synthase, as described, for example, in WO2008150486.

In a further embodiment of the invention, the further active ingredient is a glycosidase inhibitor, as described, for example, in WO2009117829, WO2009155753.

In another embodiment, the further active ingredient is an ingredient from the plant *Hoodia Gordonii*, as described in US2009042813, EP2044852.

In one embodiment, the further active ngredient is an antidiabetic, for example D-tagatose.

In one embodiment, the further active ingredient is a zinc complex of curcumin, as described in WO2009079902.

In one embodiment, the further active ingredient is an inhibitor of the "cAMP response element binding protein" (CREB), as described in WO2009143391.

In another embodiment, the further active ingredient is an antagonist of the bradykinin B1 receptor, as described in WO2009124746.

In a further embodiment, the further active ingredient is a compound which is capable of modulating diabetic peripheral neuropathy (DPN). Such modulators are, for example, FK-1706 or SB-509, or those as described in WO1989005304, WO2009092129, WO2010002956.

In one embodiment, the further active ingredient is a compound which is capable of modulating diabetic nephropathy. Such compounds are described, for example, in WO2009089545, WO2009153261.

In one embodiment, the further active ingredient is an inhibitor (e.g. an anti-CD38 antibody) of CD38, as described in US2009196825.

In one embodiment, the further active ingredient is an inhibitor of human fibroblast growth factor receptor 4 (FGFR4), as described, for example, in WO2009046141.

In a further embodiment of the invention, the further active ingredient is a compound which protects the beta cell, for example 14-alpha-lipolyl-andrographolide (AL-1).

In yet another embodiment of the invention, the further active ingredient is the INGAP (islet neogenesis associated protein) peptide, a peptide which reestablishes insulin production in patients with diabetes mellitus.

In one embodiment of the invention, the further active ingredient is a modulator of the CFTR (cystic fibrosis transmembrane conductance regulator), as described, for example, in US2009246137, US2009264433, US2009264441, US2009264471, US2009264481, US2009264486, WO2010019239.

In one embodiment of the invention, the further active ingredient is a compound which stimulates/modulates insulin release, for example those as described in WO2009109258, WO2009132739, US2009281057, WO2009157418

In one embodiment of the invention, the further active ingredient is an extract from Hippophae rhamnoides, as described, for example, in WO2009125071.

In one embodiment of the invention, the further active ingredient is an from Huanglian and Ku Ding Cha, as described, for example, in WO2009133458.

In another embodiment, the further active ingredient is a root extract from Cipadessa baccifera, as described in US2009238900.

In one embodiment of the invention, the further active ingredients are borapetoside A and/or borapetoside C, which can be isolated from the plant SDH-V, a species of Tinospora crispa, as described, for example, in US2010016213.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered within the scope of protection conferred by the present invention.

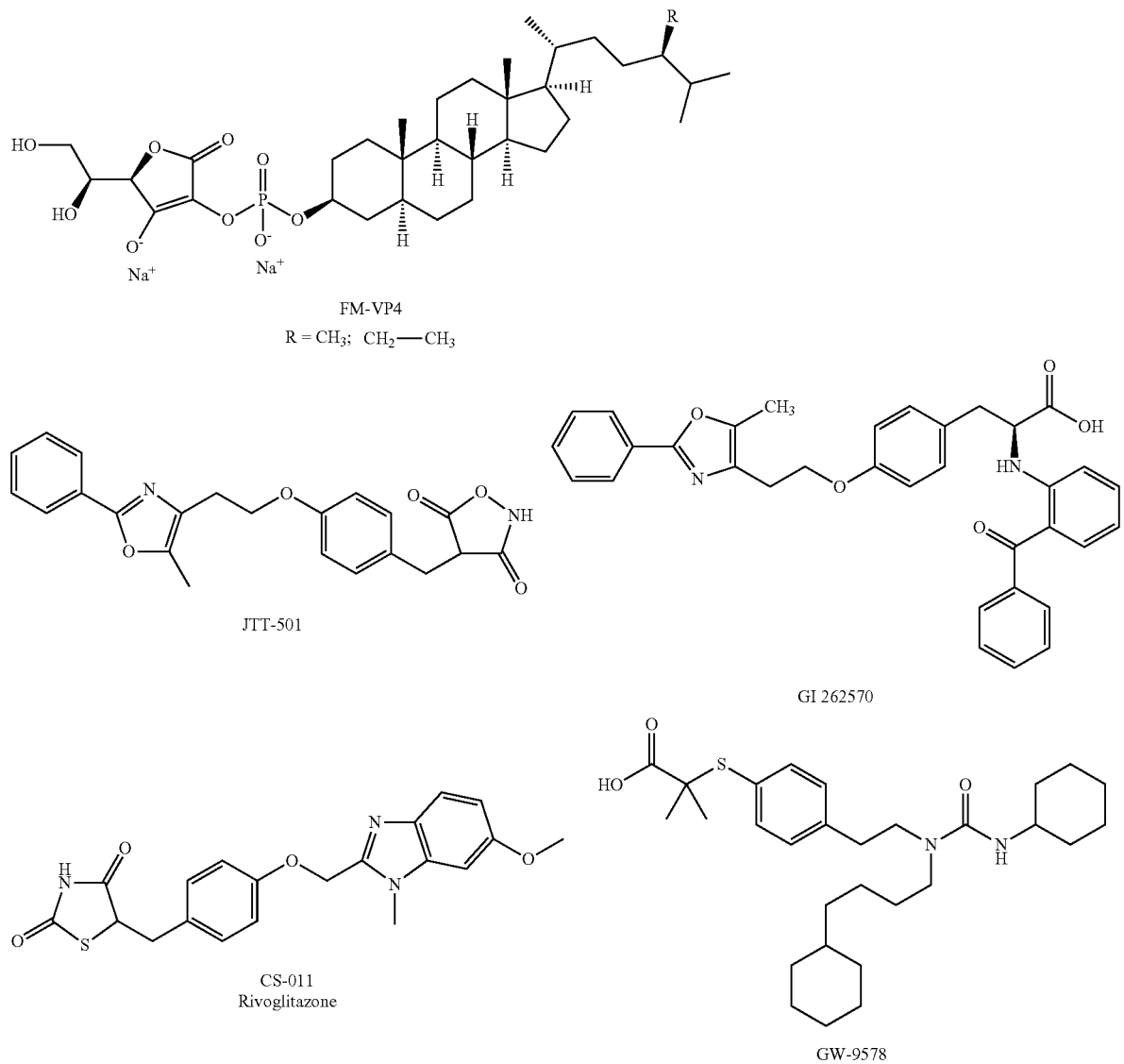

FM-VP4
R = CH$_3$; CH$_2$—CH$_3$

JTT-501

GI 262570

CS-011
Rivoglitazone

GW-9578

-continued
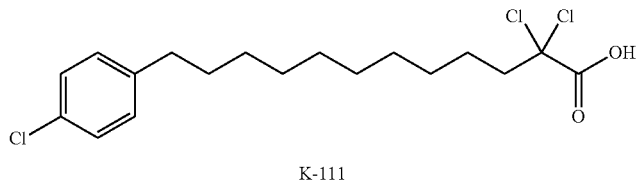
K-111
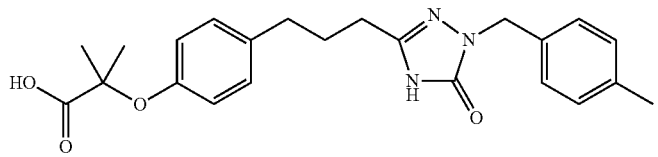
LY-518674
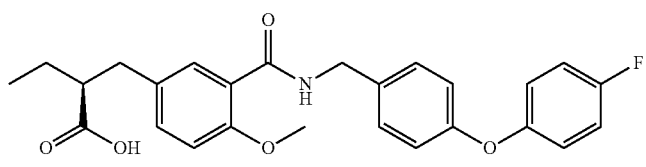
KRP-101
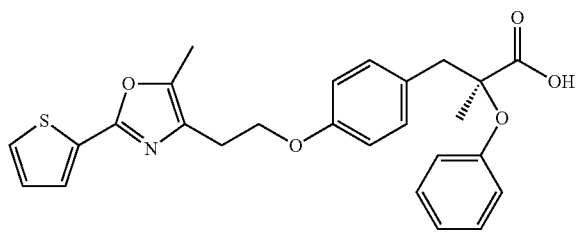
LY-510929
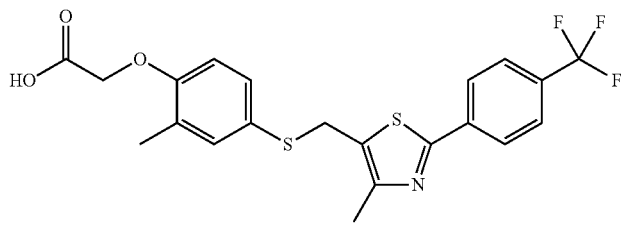
GW-501516
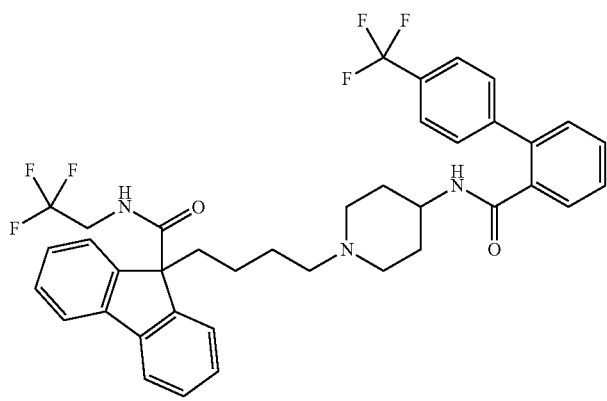
BMS-201038

-continued
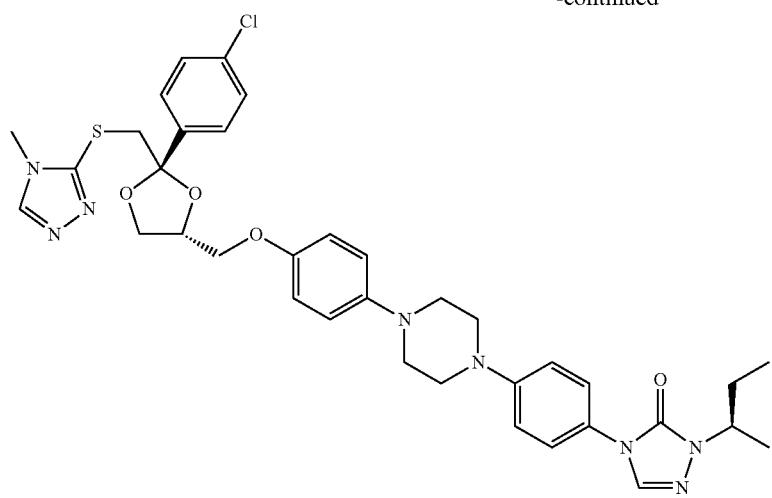
R-103757
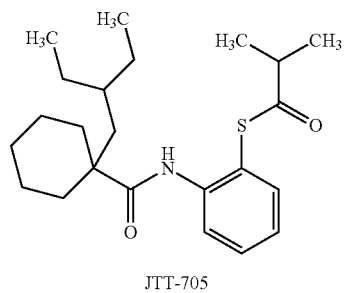
JTT-705
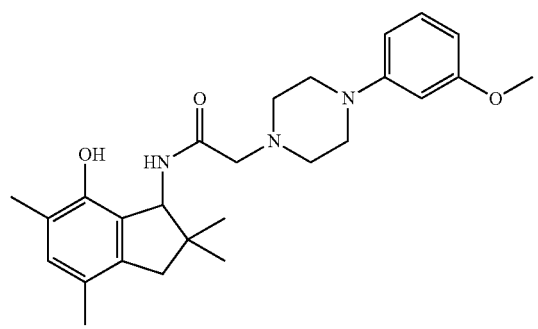
OPC-14117
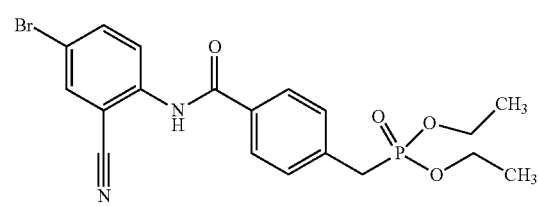
NO-1886
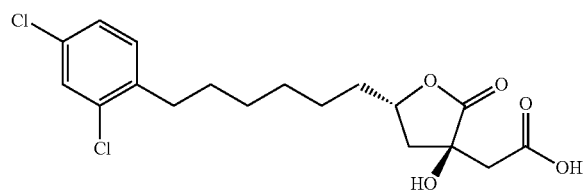
SB-204990
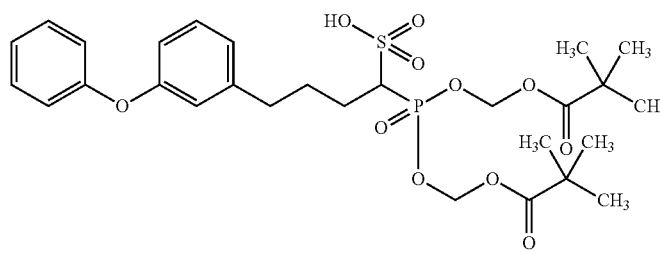
BMS-188494
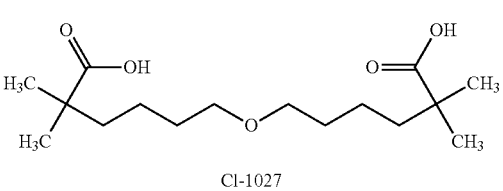
CI-1027
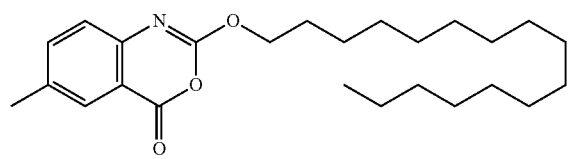
ATL-962

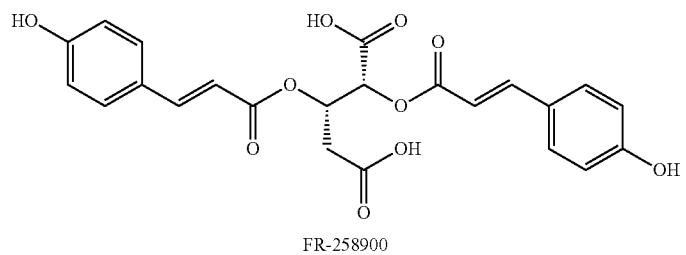
FR-258900
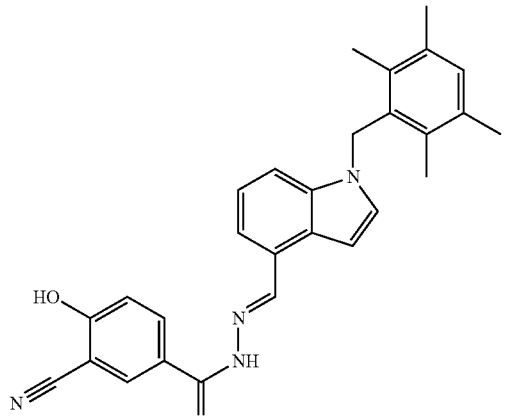
NNC-25-2504
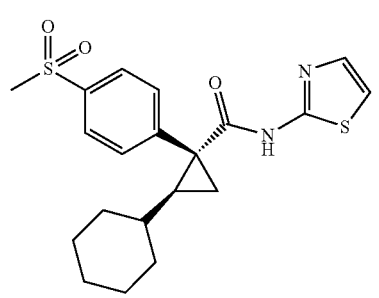
LY-2121260
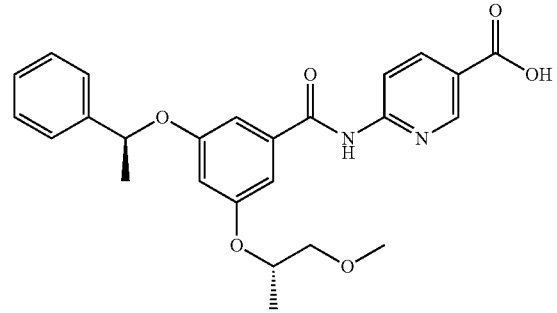
GKA-50
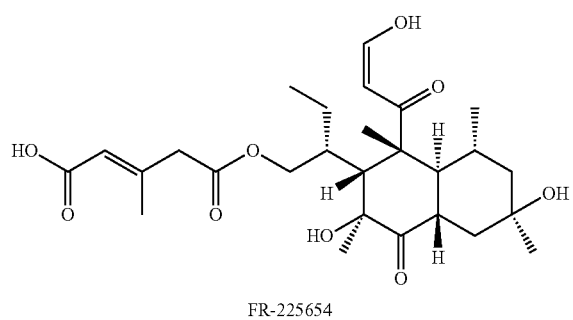
FR-225654
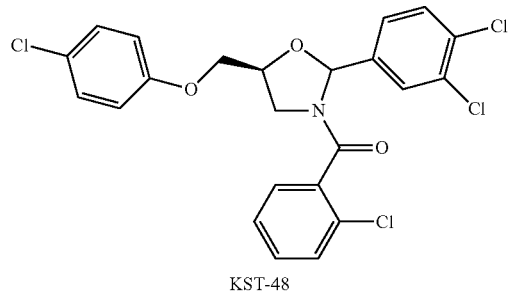
KST-48
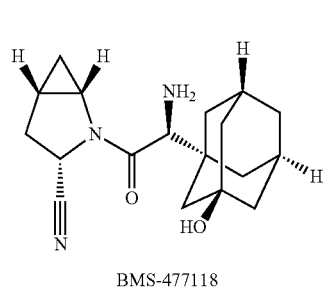
BMS-477118
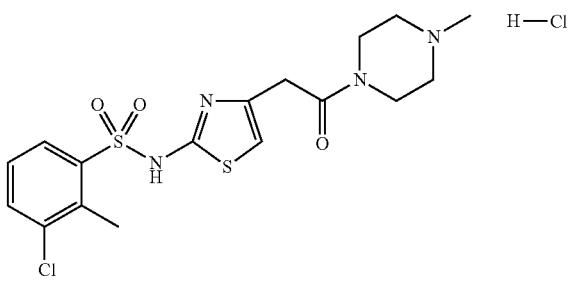
BVT-2733

-continued
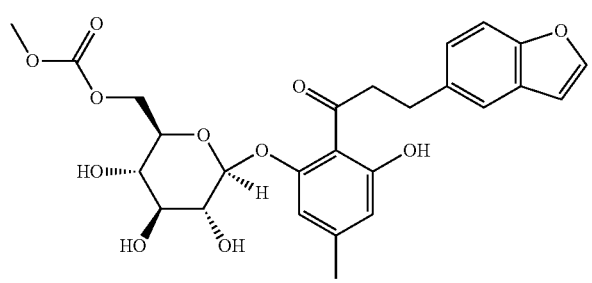
T-1095
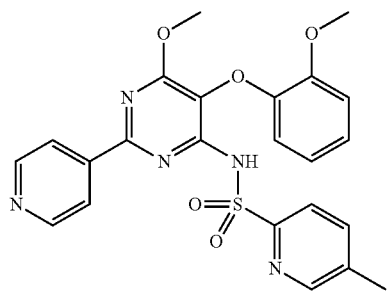
SPP-301
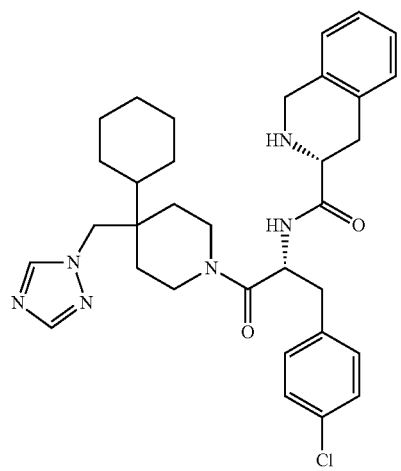
THIQ
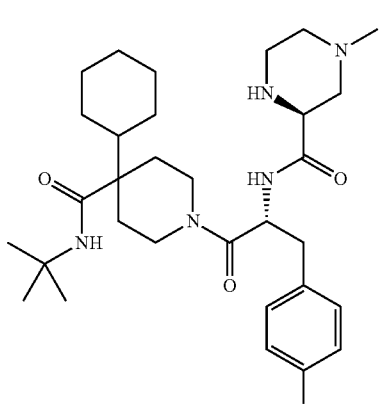
MB243
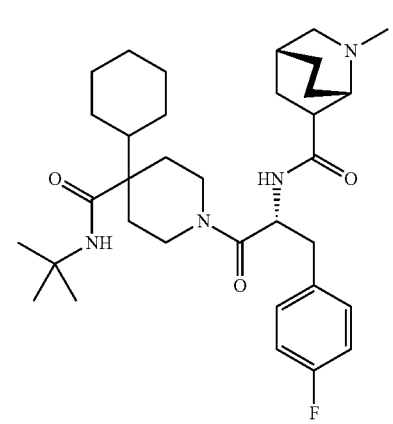
RY764
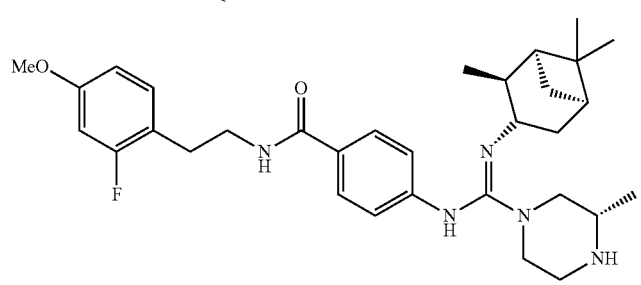
CHIR-785
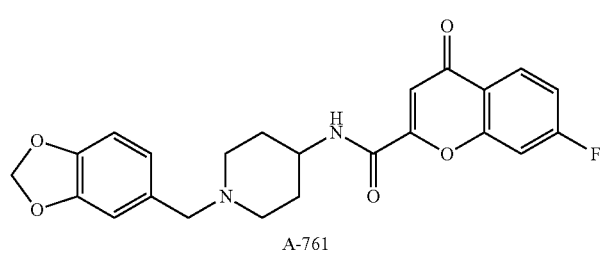
A-761
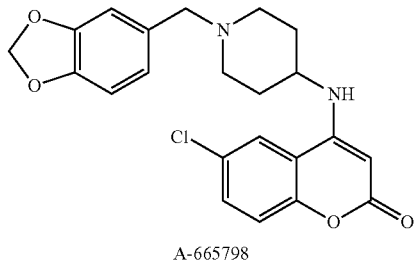
A-665798
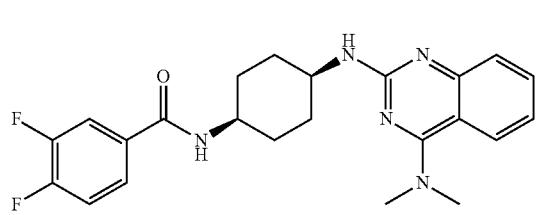
ATC-0175
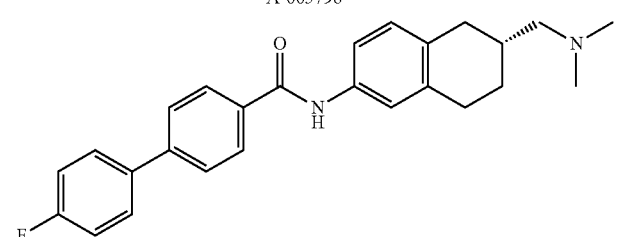
T-226296

-continued
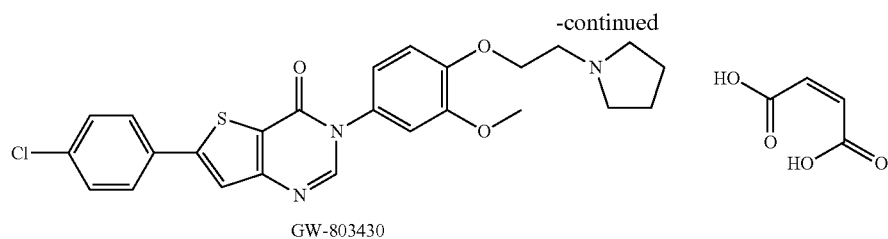
GW-803430
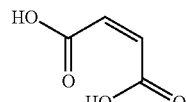
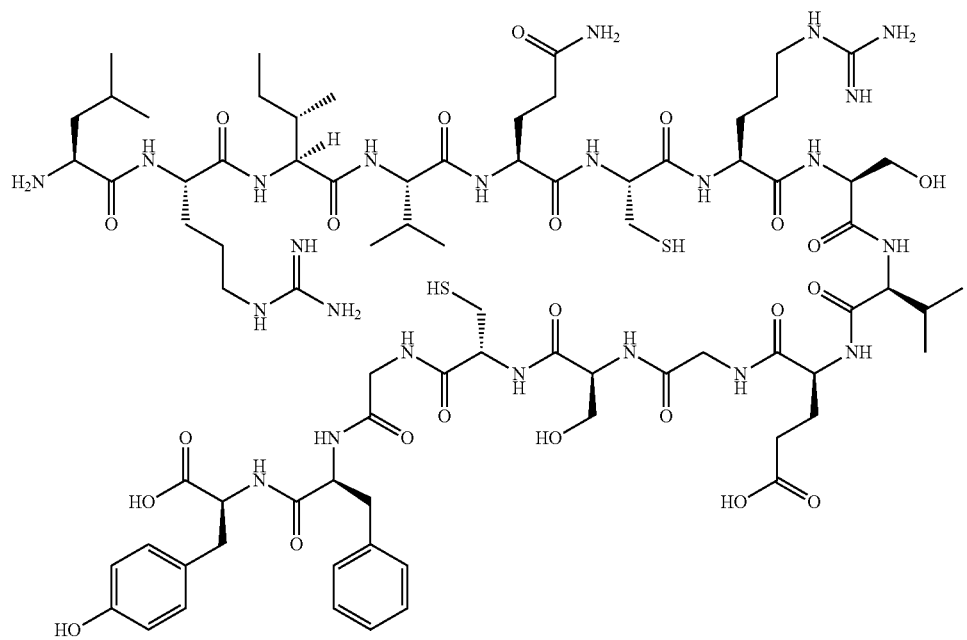
AOD-9604
Taspoglutide
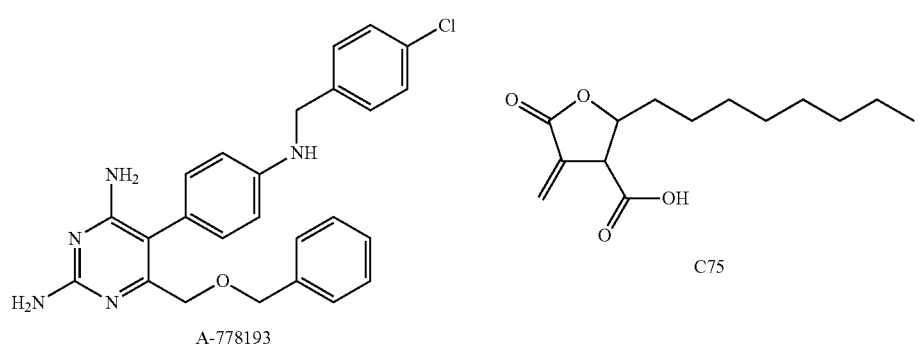
A-778193
C75
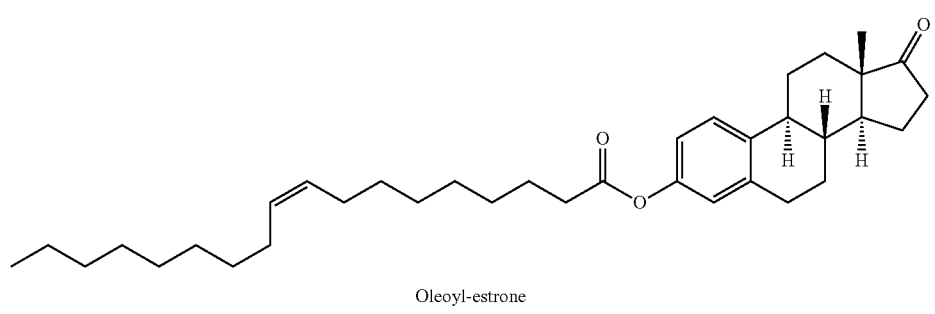
Oleoyl-estrone -continued
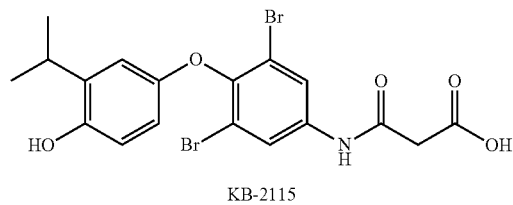
KB-2115
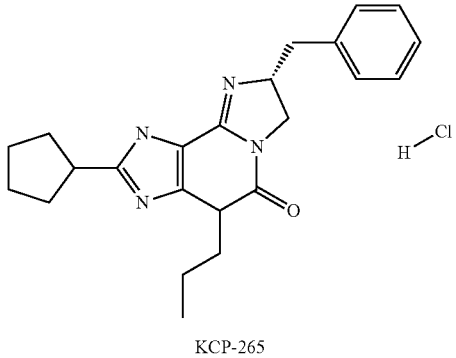
KCP-265
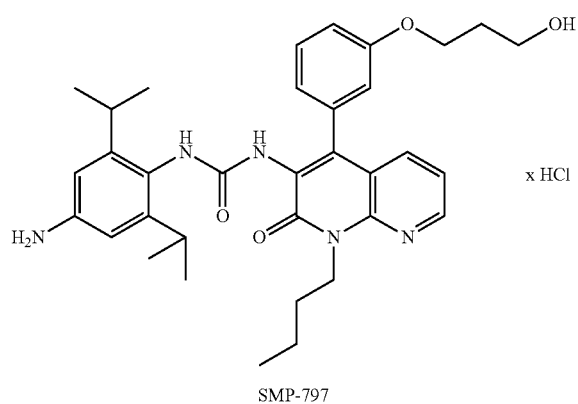
SMP-797
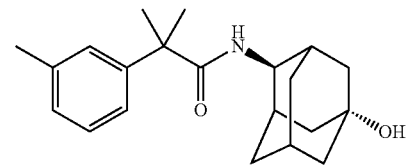
JNJ-25918646
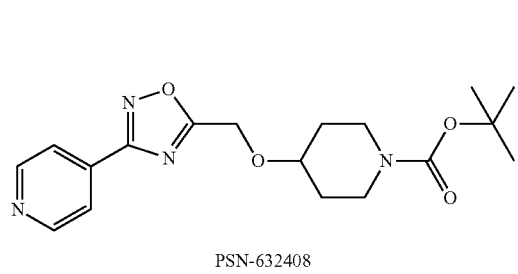
PSN-632408
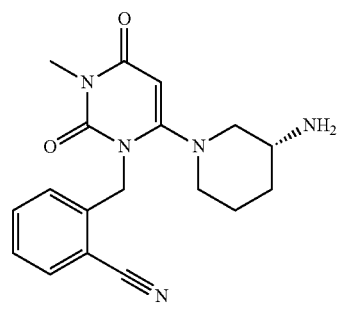
SYR-322
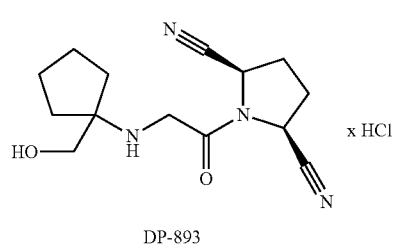
DP-893
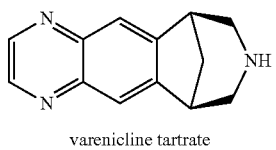
varenicline tartrate
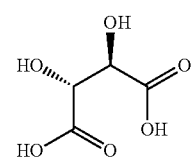
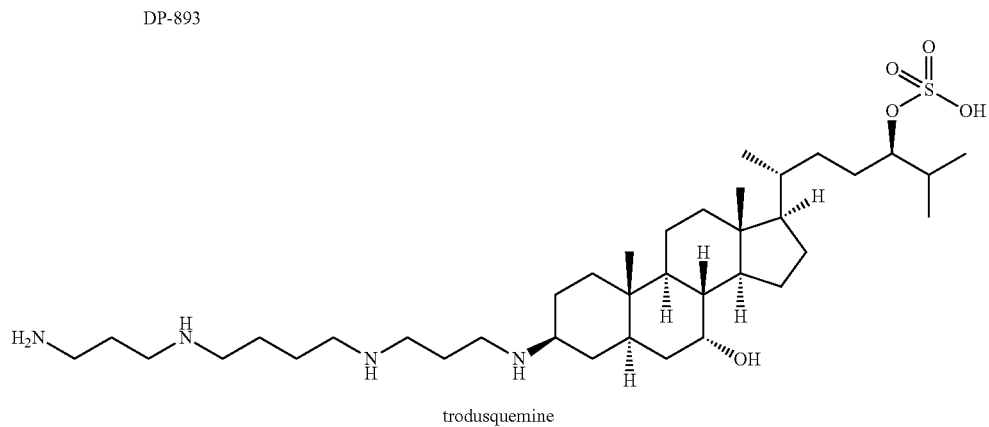
trodusquemine -continued
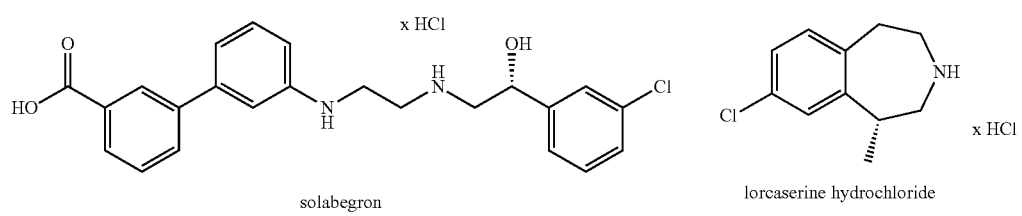
solabegron
lorcaserine hydrochloride
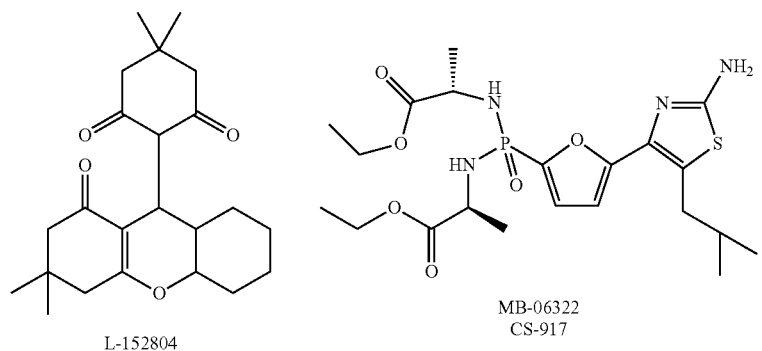
L-152804
MB-06322
CS-917
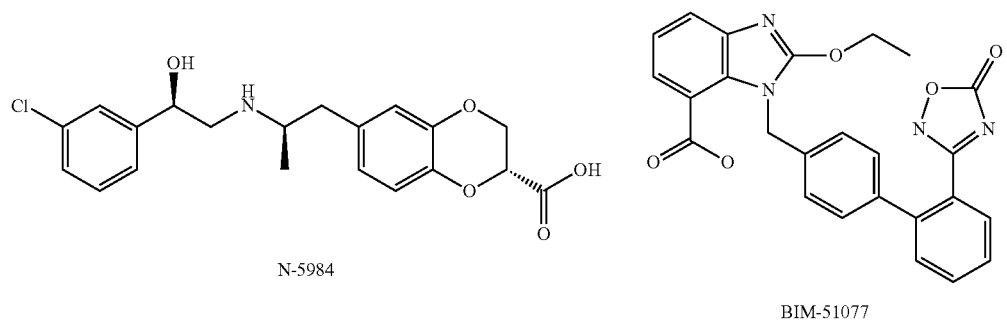
N-5984
BIM-51077
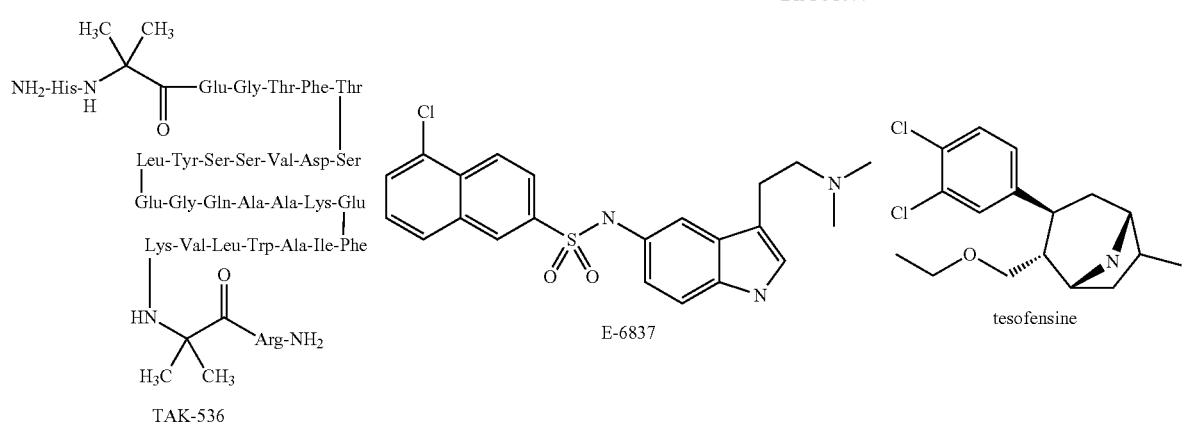
TAK-536
E-6837
tesofensine
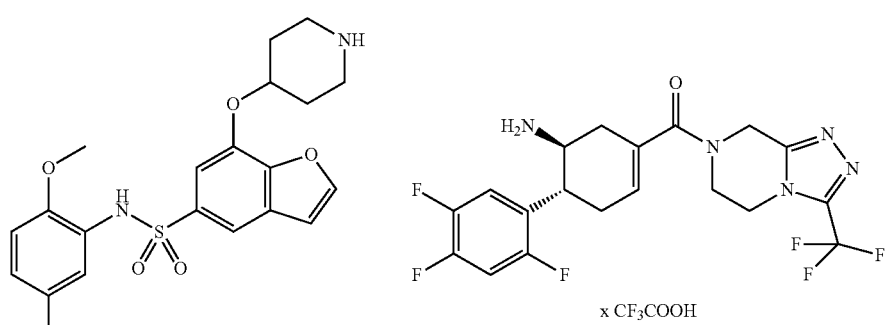
BVT-74316
ABT-341

-continued
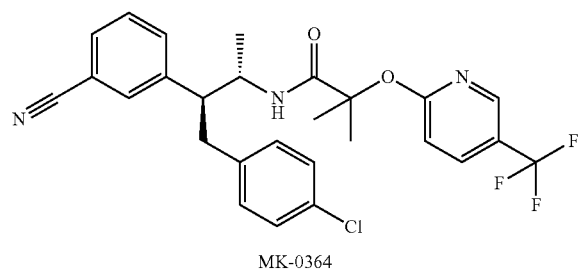
MK-0364
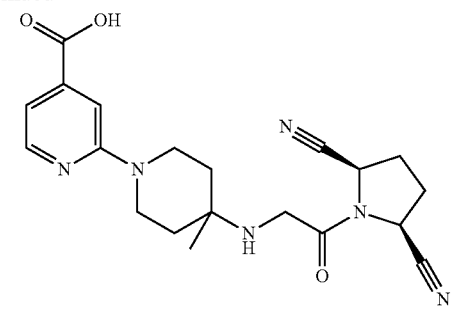
x 2 CF₃COOH
ABT-279
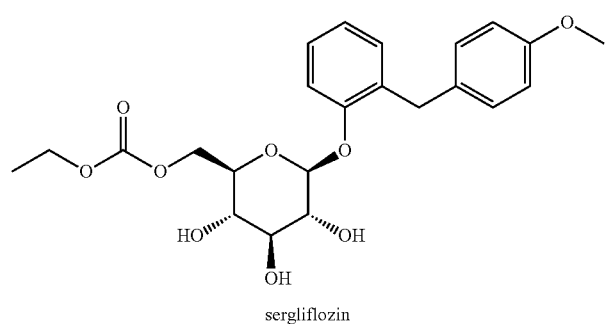
sergliflozin
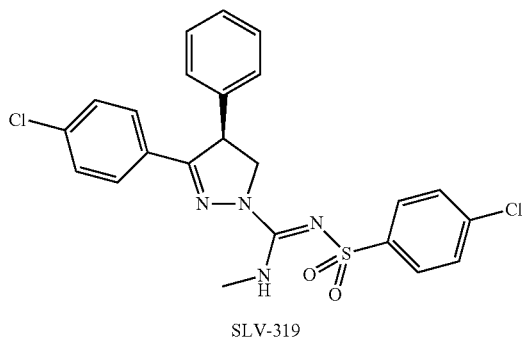
SLV-319
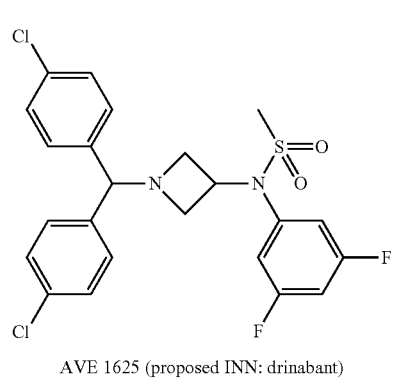
AVE 1625 (proposed INN: drinabant)
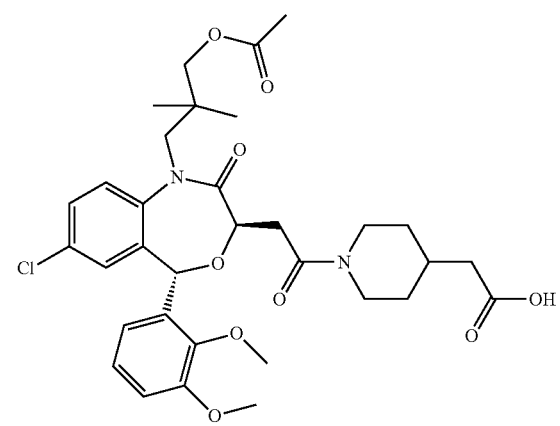
TAK-475 (lapaquistat acetate)
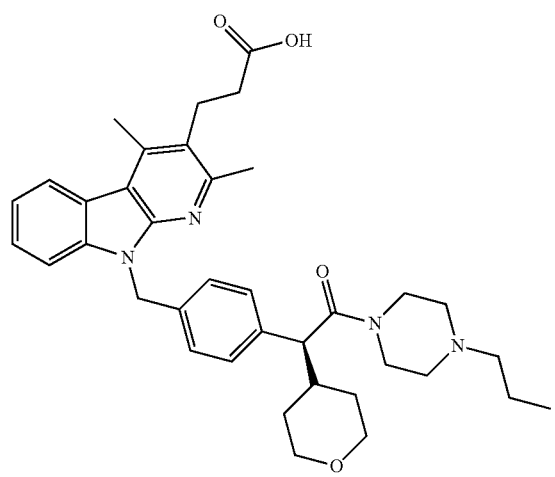
AS-1552133
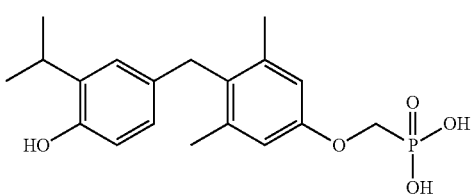
MB-07344

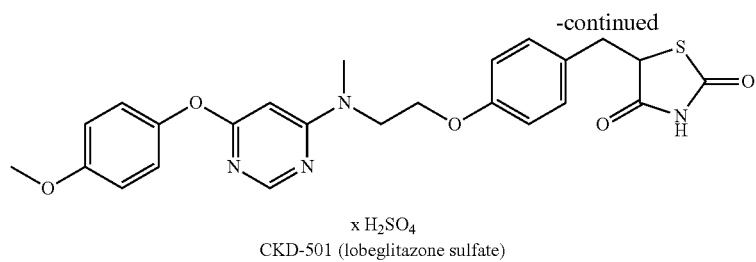
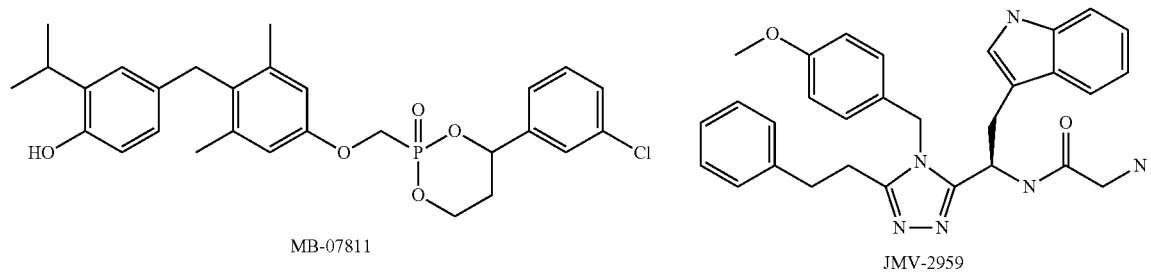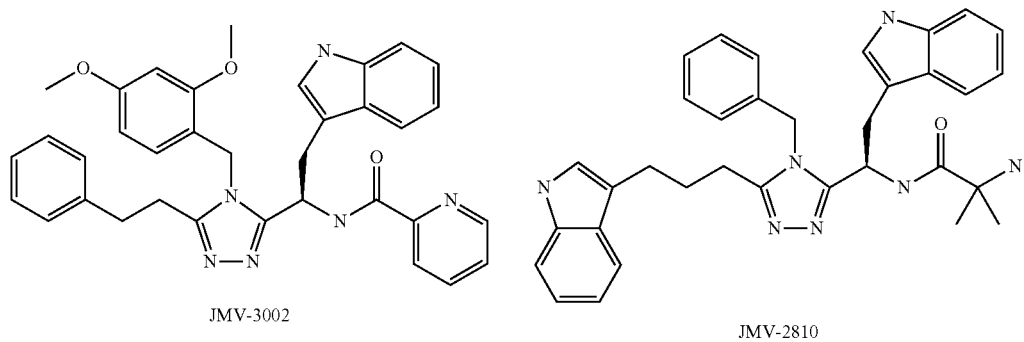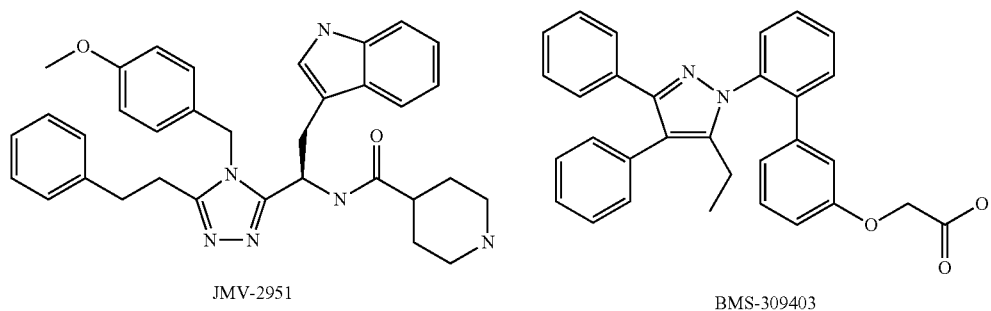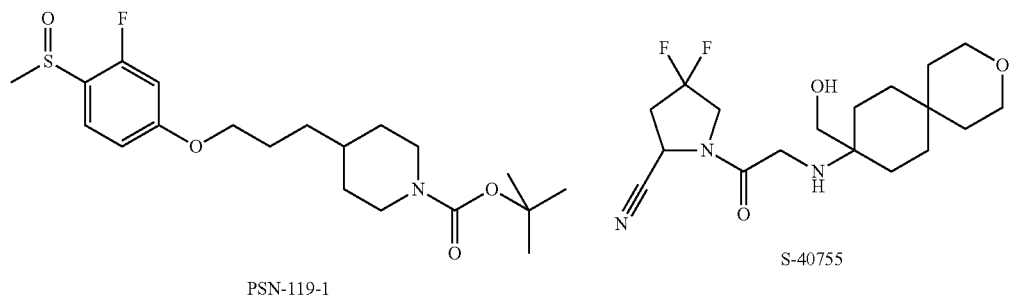

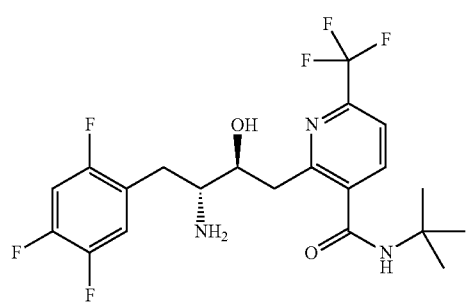
LY-2463665
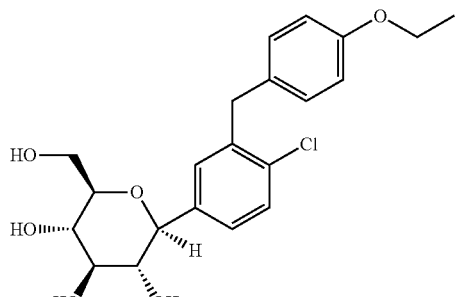
dapagliflozin, BMS-512148
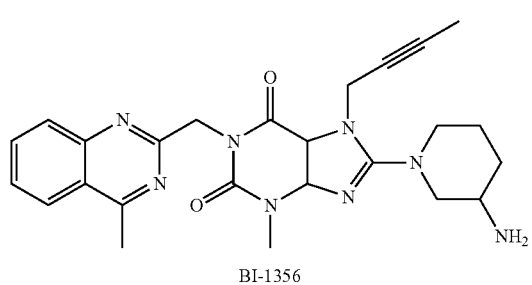
BI-1356
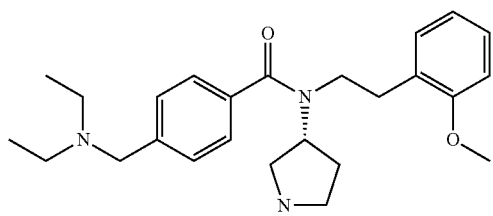
PF-429242
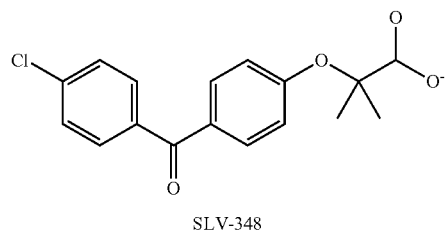
SLV-348
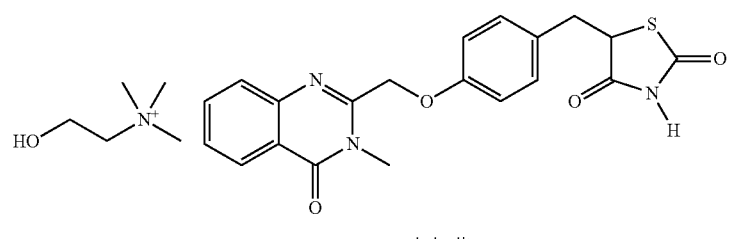
balaglitazone
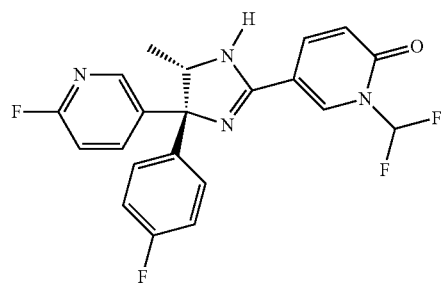
"NPY-5-BY"
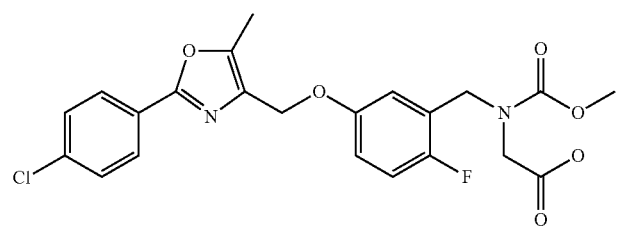
BMS-711939
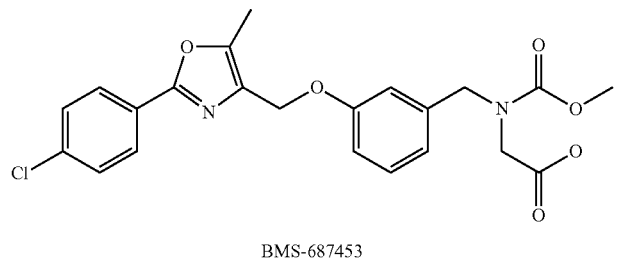
BMS-687453
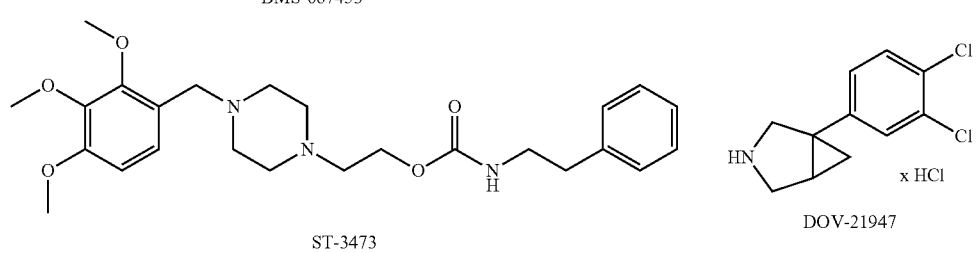
ST-3473
DOV-21947

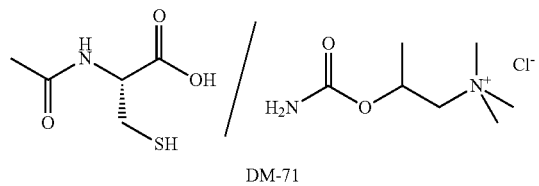
DM-71
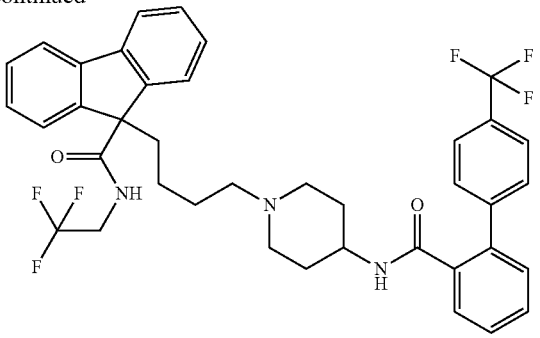
AEGR-733
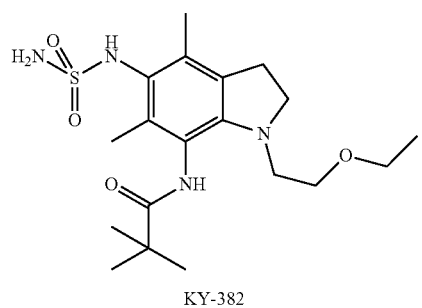
KY-382
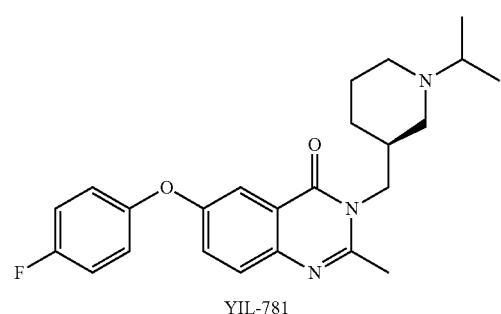
YIL-781
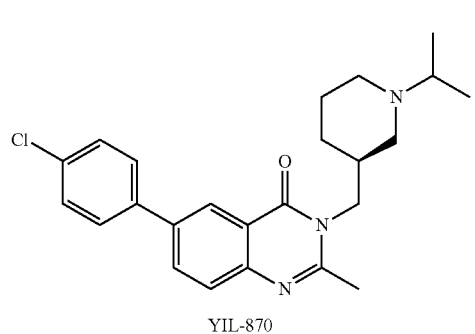
YIL-870
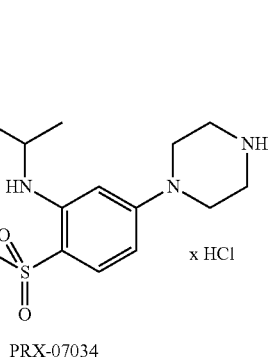
PRX-07034
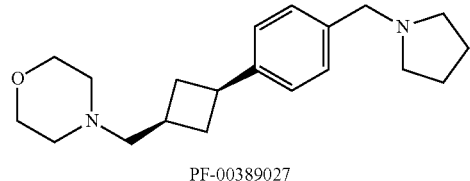
PF-00389027
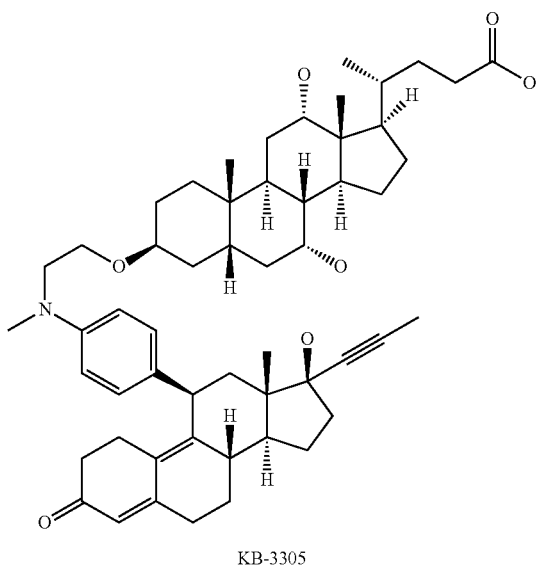
KB-3305

-continued
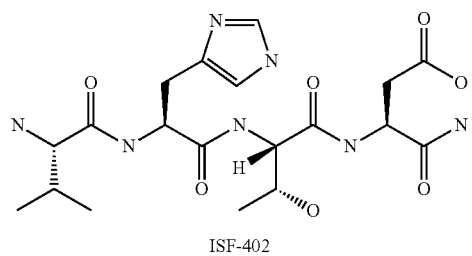
ISF-402
SRT-1720
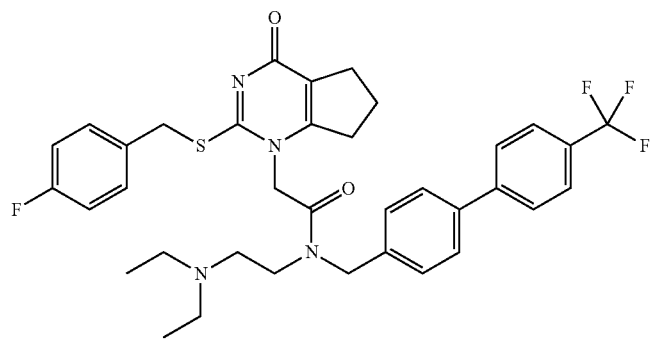
darapladib
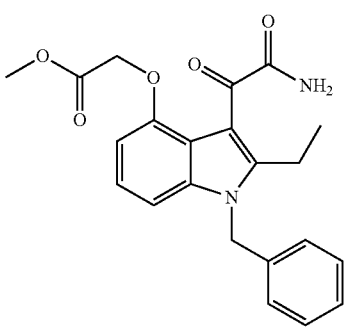
A-002
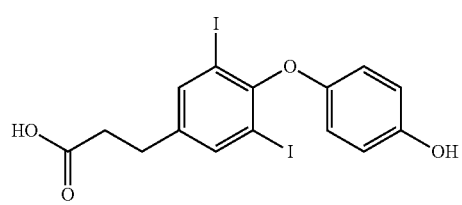
DITPA
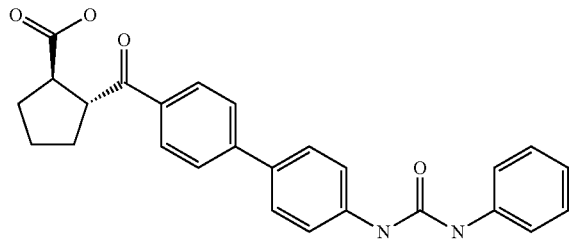
DGAT-1 inhibitor from WO2007137103
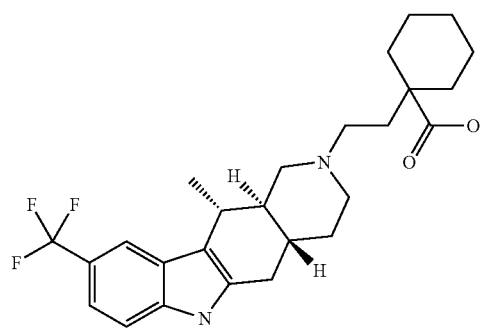
AMG-071
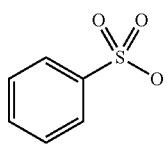
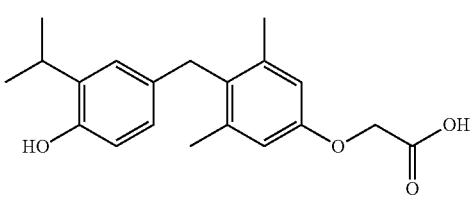
sobetirome
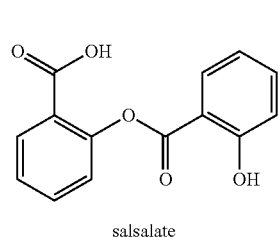
salsalate
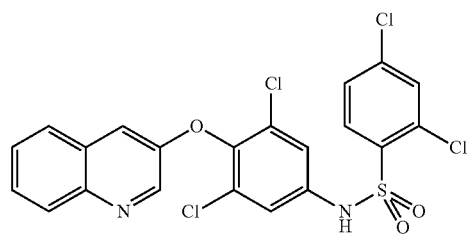
INT-131

-continued
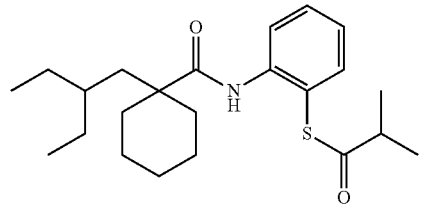
dalcetrapib
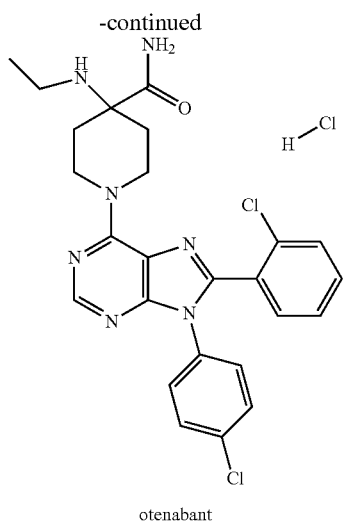
otenabant
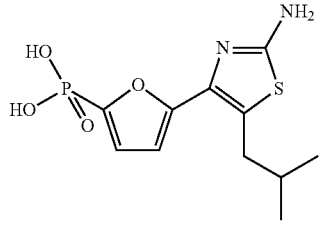
MB-07229
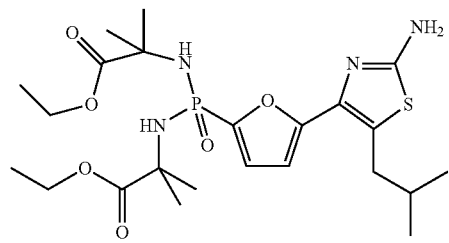
MB-07803
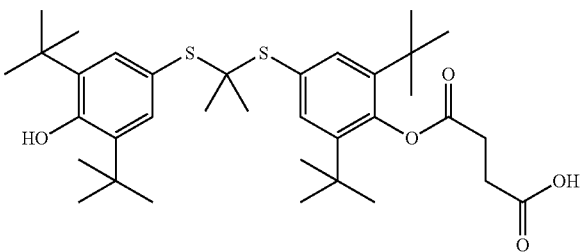
succinobucol
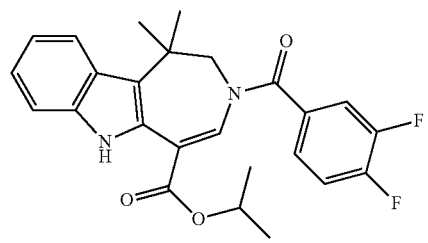
WAY-362450
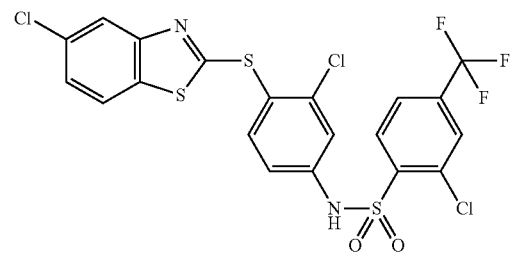
T-2384
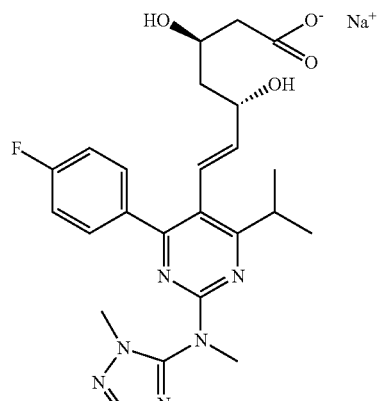
BMS-644950
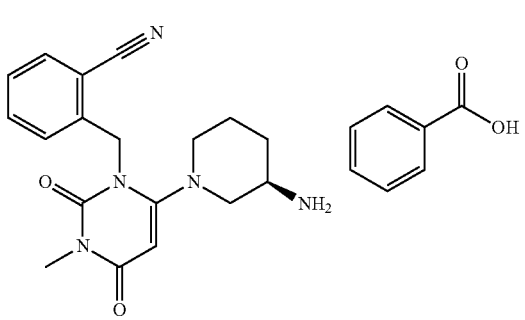
alogliptin benzoate -continued
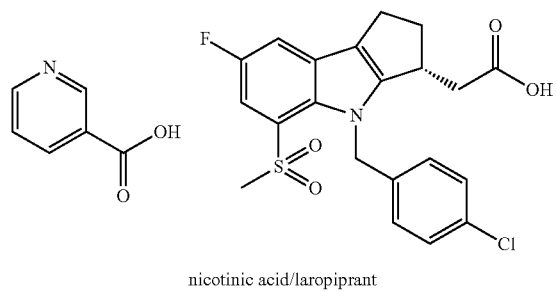
nicotinic acid/laropiprant
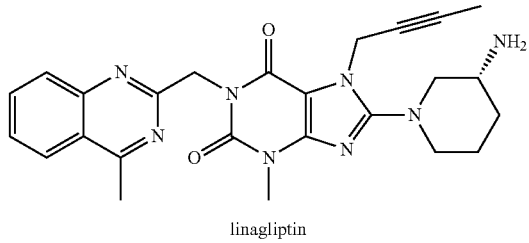
linagliptin
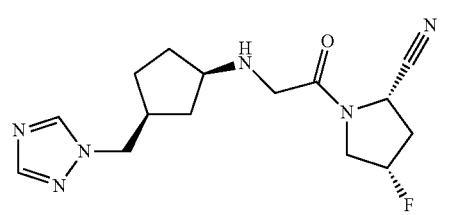
melogliptin
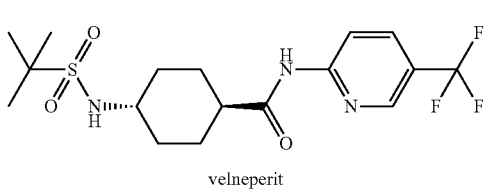
velneperit
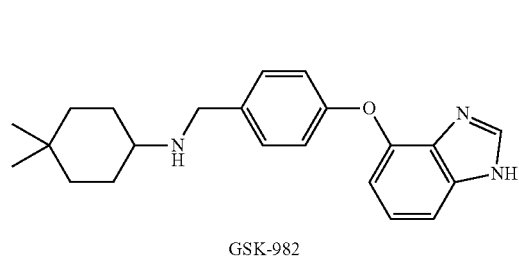
GSK-982
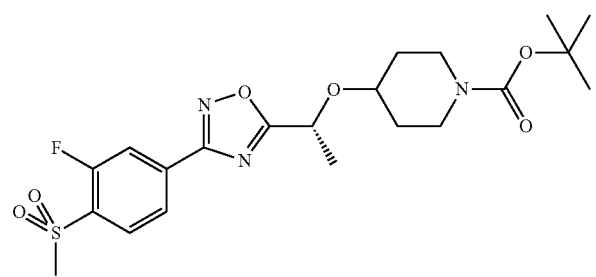
PSN-119-2
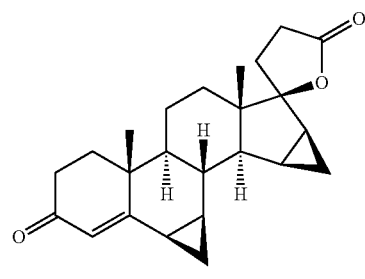
drospirenone
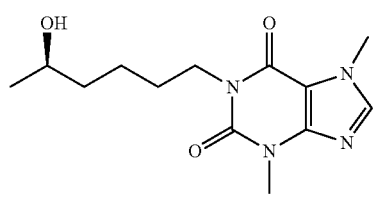
lisofylline
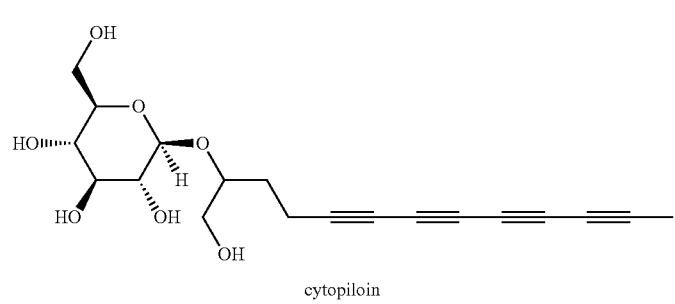
cytopiloin
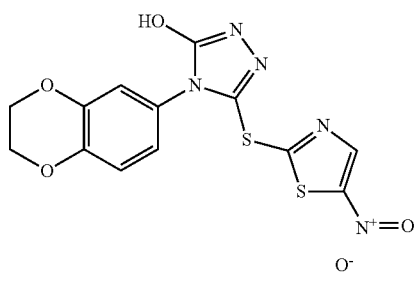
BI-78D3

-continued
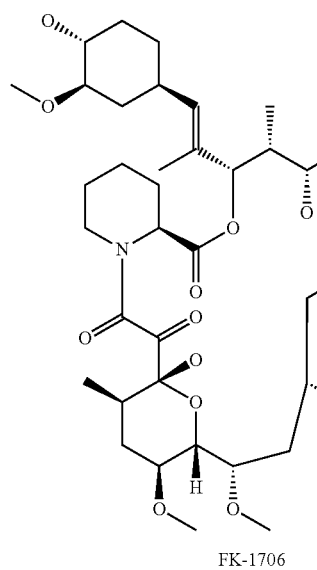
FK-1706
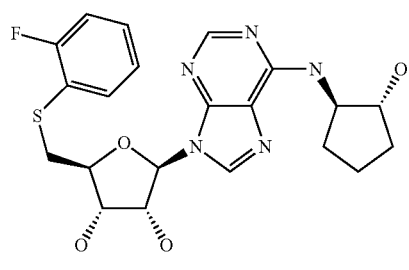
CVT-3619
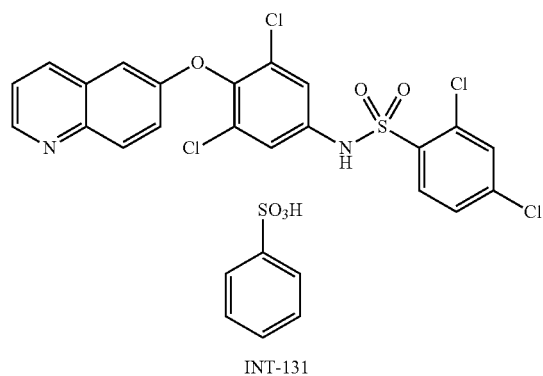
INT-131
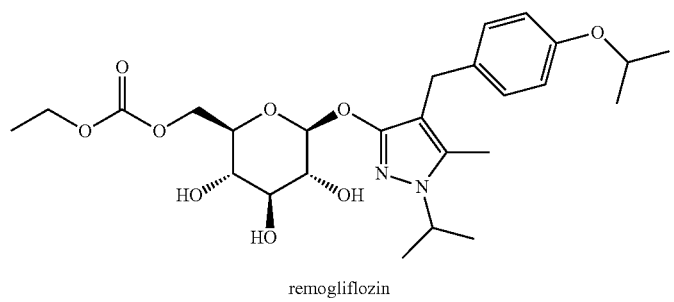
remogliflozin
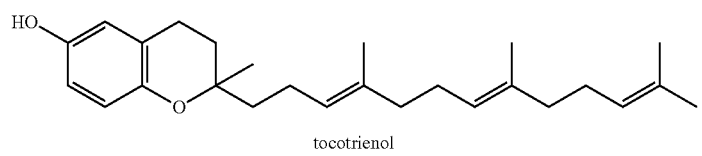
tocotrienol -continued
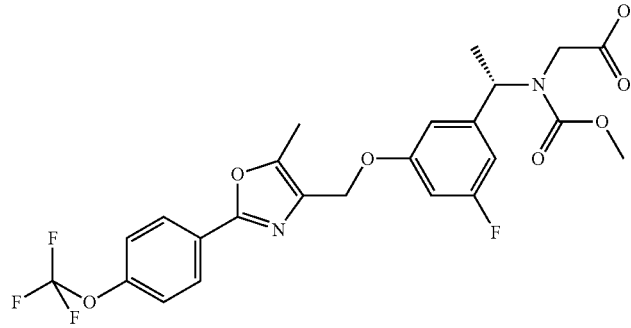
BMS-759509
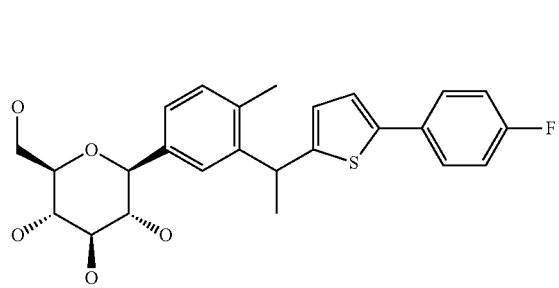
canagliflozin
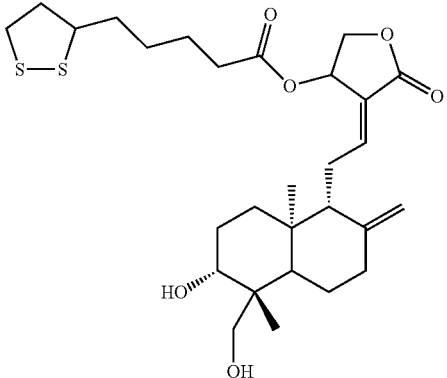
14-alpha-lipolyl-andrographolide (AL-1)
fatostatin
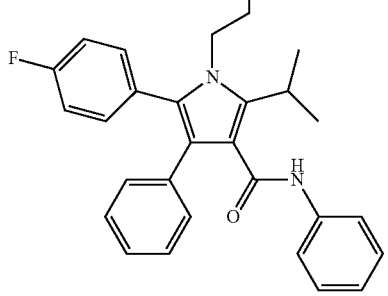
NCX-6560
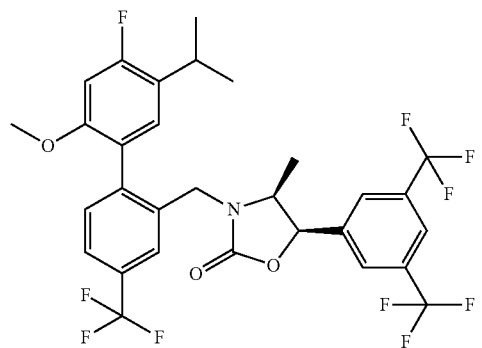
anacetrapib
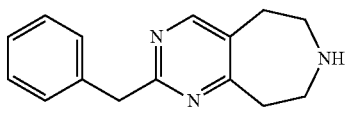
PF-3246799

Also suitable are the following active ingredients for combination preparations:
all antiepileptics specified in the Rote Liste 2010, chapter 15;
all antihypertensives specified in the Rote Liste 2010, chapter 17;
all hypotonics specified in the Rote Liste 2010, chapter 19;
all anticoagulants specified in the Rote Liste 2010, chapter 20;
all arteriosclerosis drugs specified in the Rote Liste 2010, chapter 25;
all beta receptors, calcium channel blockers and inhibitors of the renin angiotensin system specified in the Rote Liste 2010, chapter 27;
all diuretics and perfusion-promoting drugs specified in the Rote Liste 2010, chapter 36 and 37;
all withdrawal drugs/drugs for the treatment of addictive disorders specified in the Rote Liste 2010, chapter 39;
all coronary drugs and gastrointestinal drugs specified in the Rote Liste 2010, chapter 55 and 60;
all migraine drugs, neuropathy preparations and Parkinson's drugs specified in the Rote Liste 2010, chapter 61, 66 and 70.

It will be appreciated that every suitable combination of the compounds of the invention with one or more of the aforementioned compounds and optionally one or more other pharmacologically active substances is considered to be covered within the scope of protection conferred by the present invention.

The examples adduced hereinafter serve to illustrate the invention, but without restricting it.

The efficacy of the compounds was tested as follows:
In Vitro FLIPR Assay with Recombinant Cells which Express the GPCR GPR40

Function-testing assays were performed by means of the FLIPR technique ("Fluorescence Imaging Plate Reader", Molecular Devices Corp.). For this purpose, agonist-induced changes were determined in the intracellular concentration of $Ca^{2+}$ in recombinant HEK293 cells which expressed the GPCR GPR40.

For the studies, cells were sown into 96-well microtiter plates (60 000 cells/well) and left to grow overnight. The medium was removed and the cells were incubated in buffer which contains the fluorescent dye Fluo-4. After this loading with dye, the cells were washed, test substance was added and changes were measured in the intracellular $Ca^{2+}$ concentration in the FLIPR instrument. Results were presented as the percentage change relative to the control (0%: no test substance added; 100%: 10 µM reference agonist linoleic acid added) and used to calculate dose/effect curves, and $EC_{50}$ values were determined.

TABLE 2

| Biological activity | |
|---|---|
| Ex. | Rat $EC_{50}$ [µM] |
| 1 | 0.11 |
| 2 | 4.61 |
| 3 | 0.13 |
| 4 | 0.28 |
| 5 | 0.18 |
| 6 | 0.44 |
| 7 | 0.05 |
| 8 | 0.06 |
| 9 | 0.35 |

It can be seen from the table that the compounds of the formula I activate the GPR40 receptor and are thus very suitable for treatment of hyperglycemia and of diabetes. The compounds of the formula I increase insulin excretion (see Itoh et al., Nature 2003, 422, 173-176).

Due to the activation of the GPR40 receptor, the compounds of the formula I can also be employed for treatment or prevention of further disorders.

TABLE 1

I

| Ex. | R1 | R2 | R10 | R3 | R4 | X | B1 | B2 | B3 | B4 | n |
|---|---|---|---|---|---|---|---|---|---|---|---|
| 1 | —CH₃ | H | H | —CH₃ | CH₃ | — | CH | C(Br) | CH | CH | 1 |
| 2 | —CH₃ | H | H | —CH₃ | —CH₃ | — | CH | CH | C(Br) | CH | 1 |
| 3 | —CH₃ | H | H | —CH₃ | —CH₃ | — | CH | C(CF₃) | CH | CH | 1 |
| 4 | —CH₃ | H | H | —CH₃ | —CH₃ | —O— | CH | C(Br) | CH | CH | 1 |
| 5 | —CH₃ | H | H | —CH₂CH₃ | —CH₂CH₃ | — | CH | C(Br) | CH | CH | 1 |
| 6 | —CH₃ | H | H | H | H | —C(CH₃)₂— | CH | C(Br) | CH | CH | 1 |
| 7 | —CH₃ | H | H | — | — | S | CH | CH | CH | CH | 0 |
| 8 | —CH₃ | H | H | —CH₃ | —CH₃ | —O— | CH | CH | CH | CH | 1 |
| 9 | —CH₃ | H | H | —CH₃ | —CH₃ | —O— | CH | CH | CH | N | 1 |
| 10 | —CH₃ | H | H | —CH₃ | —CH₃ | —O— | CH | CH | C(CH₃) | CH | 1 |

The compounds of the present invention are especially suitable for treatment and/or prevention of:

1. disorders of fatty acid metabolism and glucose utilization disorders
   disorders involving insulin resistance
2. Diabetes mellitus, especially type 2 diabetes, including the prevention of the sequelae associated therewith.
   Particular aspects in this context are
   hyperglycemia,
   improvement in insulin resistance,
   improvement in glucose tolerance,
   protection of the pancreatic β cells
   prevention of macro- and microvascular disorders
3. Various other conditions which may be associated with metabolic syndrome or syndrome X, such as
   increased abdominal girth
   dyslipidemia (e.g. hypertriglyceridemia and/or low HDL)
   insulin resistance
   hypercoagulability
   hyperuricemia
   microalbuminemia
   thromboses, hypercoagulable and prothrombotic states (arterial and venous)
   high blood pressure
   heart failure, for example (but not restricted to) following myocardial infarction, hypertensive heart disease or cardiomyopathy
4. Memory disorders, cognitive defects, CNS disorders such as
   age-related dementia
   Alzheimer's disease
   treatment of reduced attentiveness or wakefulness
   schizophrenia General Preparation Methods Method A This method serves to prepare the units D in which X, B1, B2, B3 and B4 are each defined as described above.

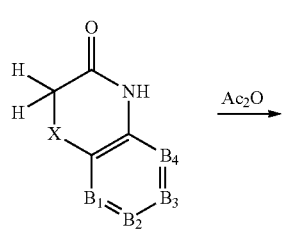

A

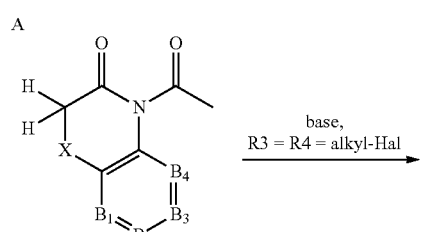

B

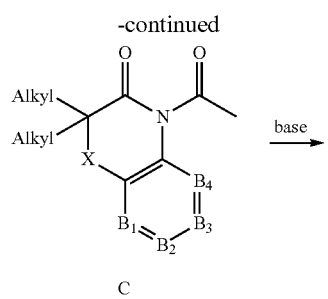

C

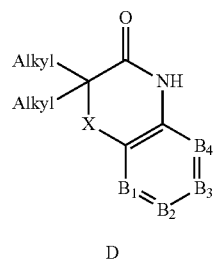

D

A compound of the general formula A in which X, B1, B2, B3 and B4 are each defined as described above is reacted in a nonpolar aprotic solvent, for example xylene, with acetic anhydride to give the N-acylated compound of the general formula B. The compound of the general formula B is reacted in a polar aprotic solvent, for example dimethylformamide, with an alkyl halide, for example methyl iodide or ethyl iodide, in the presence of a base, for example sodium hydride, to give the compound of the general formula C. The N-acetyl group of the compound of the general formula C is cleaved by reaction with a base, for example sodium hydroxide, in a polar solvent, for example ethanol, to obtain the unit of the general formula D.

Method B:

The inventive compounds of the formula I can be prepared according to the following reaction scheme:

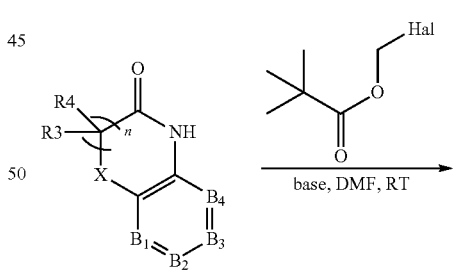

E

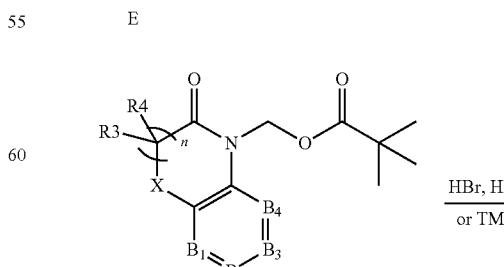

F

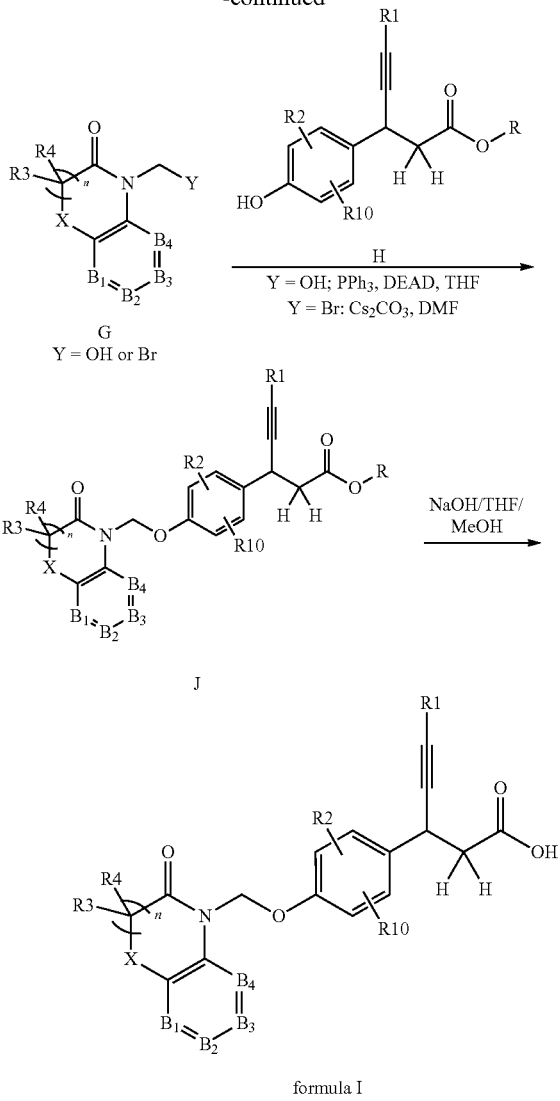

A compound of the general formula E in which n, X, B1, B2, B3 B4, R3 and R4 are each defined as described above is reacted in a polar aprotic solvent, for example dimethylformamide, with a halomethyl pivalate, for example chloromethyl pivalate in the presence of a base, for example sodium hydride, or, for example, with iodomethyl pivalate in the presence of a base, for example cesium carbonate, to give the compound of the general formula F. The pivalate group of the compound of the general formula F is cleaved, for example, by treatment with an acid, for example HBr in glacial acetic acid, to obtain the compound of the general formula G in which Y is a hydroxyl group. Alternatively, the pivalate group of the compound of the general formula F can be cleaved, for example, by treatment with trimethylsilyl bromide to obtain the compound of the general formula G in which Y is a bromide. In the case that Y is a hydroxyl group, the compound of the general formula G is reacted under Mitsunobu conditions, in the presence of, for example, triphenylphosphine and diethyl diazodicarboxylate, in an aprotic solvent, for example dichloromethane, with a compound of the general formula H in which R1, R2 and R10 are each defined as described above and R is an alkyl group, for example methyl or ethyl, to give the compound of the general formula J. In the case that Y is a bromide, the reaction of the compound of the general formula G with a compound of the general formula H to give the compound of the general formula J takes place in a polar aprotic solvent, for example dimethylformamide, in the presence of a base, for example cesium carbonate. Under the action of a base, for example sodium hydroxide, in a solvent mixture, for example methanol, tetrahydrofuran and water, the ester of the general formula J is cleaved to obtain the free carboxylic acid of the general formula I. The racemic mixture can be separated by chiral HPLC into the enantiomerically pure forms.

This method was used to prepare examples 1-9.

LIST OF ABBREVIATIONS

Ac acetyl
Bn benzyl
iBu isobutyl
tBu tert-butyl
BuLi n-butyllithium
TLC thin-layer chromatography
DEAD diethyl azodicarboxylate
DCI direct chemical ionization (in MS)
DCM dichloromethane
DMAP 4-N,N-dimethylaminopyridine
DMF N,N-dimethylformamide
DMSO dimethyl sulfoxide
EE ethyl acetate
ent enantiomer/enantiomerically pure
EI electron impact ionization (in MS)
eq equivalent
ESI electrospray ionization (in MS)
FG functional group
Hal halogen
HPLC high-pressure, high-performance liquid chromatography
LC-MS liquid chromatography-coupled mass spectrometry
m meta
Me methyl
MeOH methanol
MS mass spectrometry
Ms mesyl
NMR nuclear magnetic resonance spectroscopy
ortho
p para
Pd/C palladium on carbon
iPr isopropyl
nPr n-propyl
rac racemic racemic mixture
Rf retention time (in TLC)
reverse phase
THF tetrahydrofuran

EXPERIMENTAL

Unit Syntheses According to Method A 3,3-Dimethyl-5-trifluoromethyl-1-dihydroindol-2-one

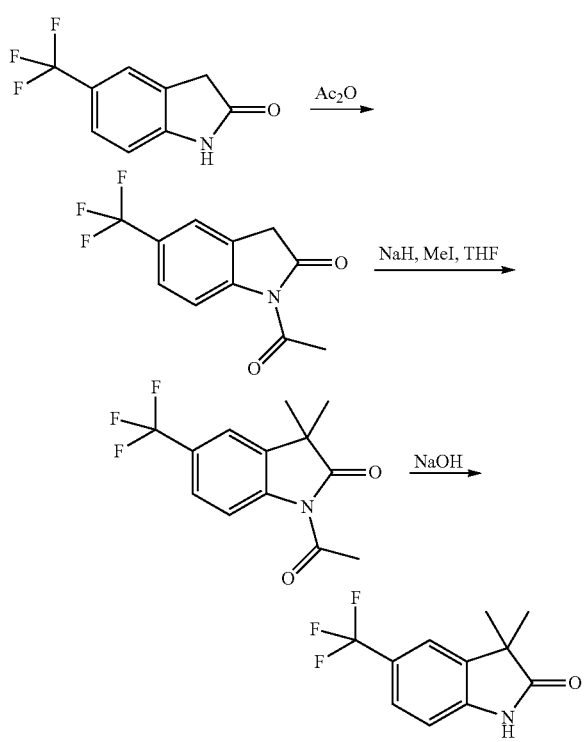

1-Acetyl-5-trifluoromethyl-1,3-dihydroindol-2-one

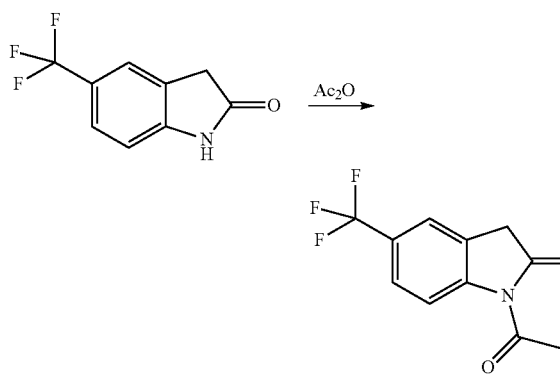

2.0 g of 5-trifluoromethyloxoindole were dissolved in 25 ml of xylene, 2.41 ml of acetic anhydride were added and the mixture was heated to boiling under reflux for 5 hours. The reaction solution was cooled to room temperature and diluted with 150 ml of ethyl acetate, and washed with 80 ml each of water, saturated sodium bicarbonate solution and saturated NaCl solution. The organic phase was dried over MgSO$_4$ and concentrated under reduced pressure. The residue was purified on silica gel with the eluent n-heptane=>n-heptane/ethyl acetate=3:1. This gave 1.74 g of 1-acetyl-5-trifluoromethyl-1,3-dihydroindol-2-one as a colorless solid.

$C_{11}H_8F_3NO_2$ (243.19), LCMS (ESI-pos): 244.1 (M+H$^+$), TLC in n-heptane/ethyl acetate=7:3 R$_f$=0.65.

1-Acetyl-3,3-dimethyl-5-trifluoromethyl-1,3-dihydroindol-2-one

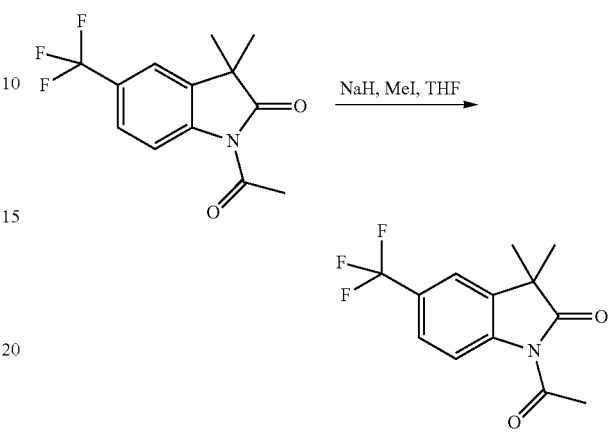

1.74 g of 1-acetyl-5-trifluoromethyl-1,3-dihydroindol-2-one were dissolved in 250 ml of dry THF. At 0° C., 716 mg of sodium hydride (60% dispersion in mineral oil) were added under argon. The reaction solution was stirred at room temperature for 10 minutes, then 1.14 ml of methyl iodide were added dropwise. The reaction solution was stirred at room temperature for two hours. A further 286 mg of sodium hydride and 0.45 ml of methyl iodide were metered in and the mixture was stirred at room temperature for a further hour. The reaction solution was quenched by adding 50 ml of saturated ammonium chloride solution and extracted with 300 ml of ethyl acetate. The organic phase was washed with 100 ml of water and 100 ml of saturated NaCl solution, dried over MgSO$_4$ and concentrated under reduced pressure. The residue was purified on silica gel with the eluent n-heptane n-heptane/ethyl acetate=1:1. This gave 464 mg of 1-acetyl-3,3-dimethyl-5-trifluoromethyl-1,3-dihydroindol-2-one.
$C_{13}H_{12}F_3NO_2$ (271.24), LCMS (ESI-pos): 272.1 (M+H$^+$), TLC in n-heptane/ethyl acetate=1:1 R$_f$=0.81.

3,3-Dimethyl-5-trifluoromethyl-1,3-dihydroindol-2-one

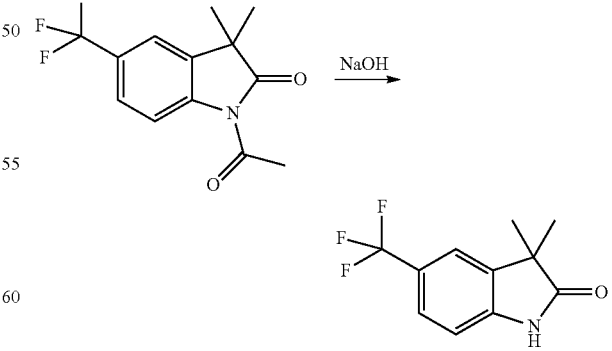

464 mg of 1-acetyl-3,3-dimethyl-5-trifluoromethyl-1,3-dihydroindol-2-one were dissolved in 4 ml of ethanol, and 1 ml of 1N sodium hydroxide solution was added. The reaction mixture was then stirred at room temperature for one hour.

The reaction solution was extracted with 80 ml of methyl tert-butyl ether. The organic phase was washed with 30 ml of water and with 30 ml of saturated NaCl solution, dried over MgSO$_4$ and concentrated under reduced pressure. This gave 354 mg of 3,3-dimethyl-5-trifluoromethyl-1,3-dihydroindol-2-one as a colorless solid.

C$_{11}$H$_{10}$F$_3$NO (229.20), LCMS (ESI-pos): 230.1 (M+H$^+$).

Example Syntheses According to Method B

Example 1

3-[4-(5-Bromo-3,3-dimethyl-2-oxo-2,3-dihydroindol-1-ylmethoxy)phenyl]hex-4-ynoic acid

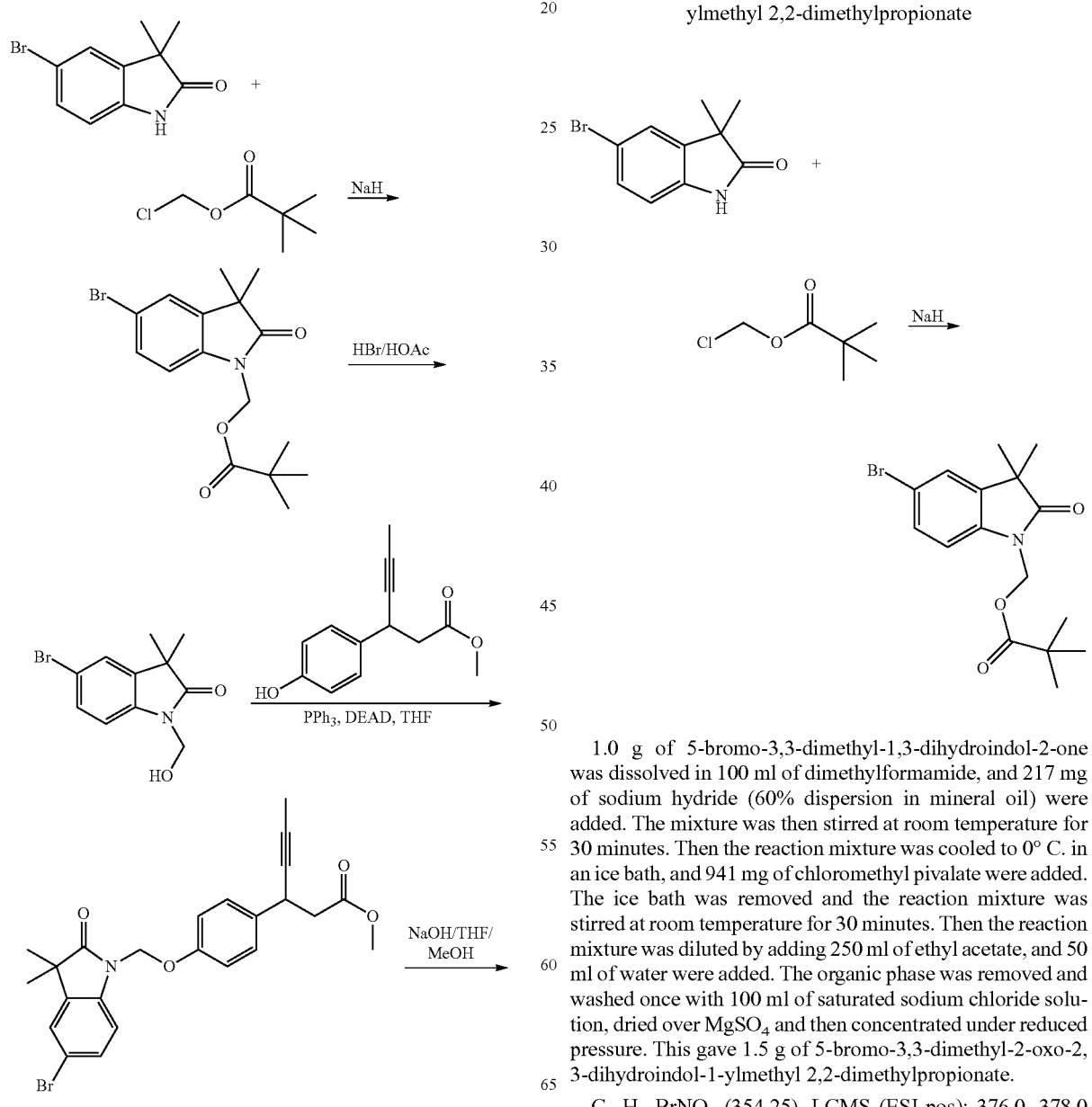

5-Bromo-3,3-dimethyl-2-oxo-2,3-dihydroindol-1-ylmethyl 2,2-dimethylpropionate

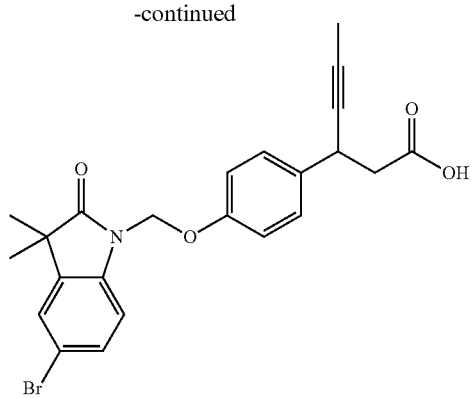

1.0 g of 5-bromo-3,3-dimethyl-1,3-dihydroindol-2-one was dissolved in 100 ml of dimethylformamide, and 217 mg of sodium hydride (60% dispersion in mineral oil) were added. The mixture was then stirred at room temperature for 30 minutes. Then the reaction mixture was cooled to 0° C. in an ice bath, and 941 mg of chloromethyl pivalate were added. The ice bath was removed and the reaction mixture was stirred at room temperature for 30 minutes. Then the reaction mixture was diluted by adding 250 ml of ethyl acetate, and 50 ml of water were added. The organic phase was removed and washed once with 100 ml of saturated sodium chloride solution, dried over MgSO$_4$ and then concentrated under reduced pressure. This gave 1.5 g of 5-bromo-3,3-dimethyl-2-oxo-2,3-dihydroindol-1-ylmethyl 2,2-dimethylpropionate.

C$_{16}$H$_{20}$BrNO$_3$ (354.25), LCMS (ESI-pos): 376.0, 378.0 (M+Na$^+$), 252.0, 254.0 (M-pivalate$^-$).

5-Bromo-1-hydroxymethyl-3-dimethyl-1,3-dihydroindol-2-one

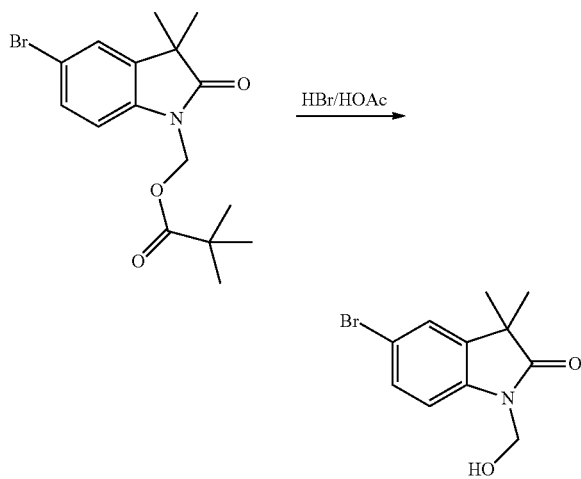

1.5 g of 5-bromo-3,3-dimethyl-2-oxo-2,3-dihydroindol-1-ylmethyl 2,2-dimethylpropionate were dissolved in 10 ml of glacial acetic acid, 2 ml of HBr/HOAc were added and the mixture was heated to 100° C. After 30 minutes, the mixture was allowed to cool to room temperature and the reaction mixture was poured onto 50 ml of ice-water. The mixture was extracted three times with 80 ml each time of ethyl acetate, and the combined organic phases were dried over MgSO$_4$ and then concentrated under reduced pressure. The residue was purified on silica gel with the n-heptane/ethyl acetate solvent mixture as a linear gradient of 100% n-heptane=>50% ethyl acetate. This gave 556 mg of 5-bromo-1-hydroxymethyl-3,3-dimethyl-1,3-dihydroindol-2-one.

$C_{11}H_{11}BrN_2$ (270.13), LCMS (ESI-pos): 252.0, 254.0 (M−H$_2$O+H$^+$), TLC in n-heptane:EA=1:1 R$_f$=0.33.

Methyl 3-[4-(5-bromo-3,3-dimethyl-2-oxo-2,3-dihydroindol-1-ylmethoxy)phenyl]hex-4-ynoate

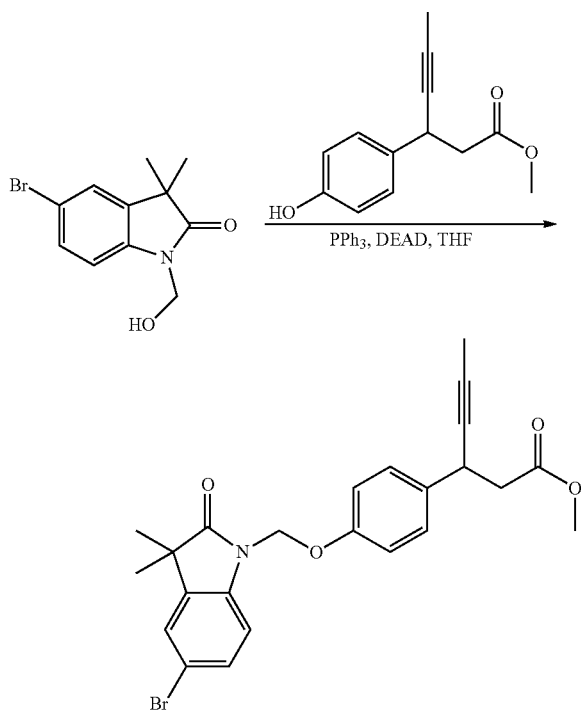

556 mg of 5-bromo-1-hydroxymethyl-3,3-dimethyl-1,3-dihydroindol-2-one, 673 mg of methyl 3-(4-hydroxyphenyl) hex-4-ynoate and 810 mg of tri-phenylphosphine were dissolved in 100 ml of tetrahydrofuran. While cooling with ice, 538 mg of diethyl azodicarboxylate was added dropwise. The ice bath was removed and the reaction mixture was stirred at room temperature for 1 hour. Then 5 ml of water were added cautiously and the reaction mixture was concentrated under reduced pressure. The residue was taken up in 50 ml of water and 50 ml of ethyl acetate. The organic phase was removed, dried over MgSO$_4$ and then concentrated under reduced pressure. The residue was purified on silica gel with the n-heptane/ethyl acetate solvent mixture as a linear gradient of 100% n-heptane=>50% ethyl acetate. This gave 730 mg of methyl 3-[4-(5-bromo-3,3-dimethyl-2-oxo-2,3-dihydroindol-1-ylmethoxy)phenyl]-hex-4-ynoate.

$C_{24}H_{24}BrNO_4$ (470.37), LCMS (ESI-pos): 470.2, 472.1 (M+H$^+$), TLC in n-heptane:EA=1:1 R$_f$=0.53.

3-[4-(5-Bromo-3,3-dimethyl-2-oxo-2,3-dihydroindol-1-ylmethoxy)phenyl]hex-4-ynoic acid

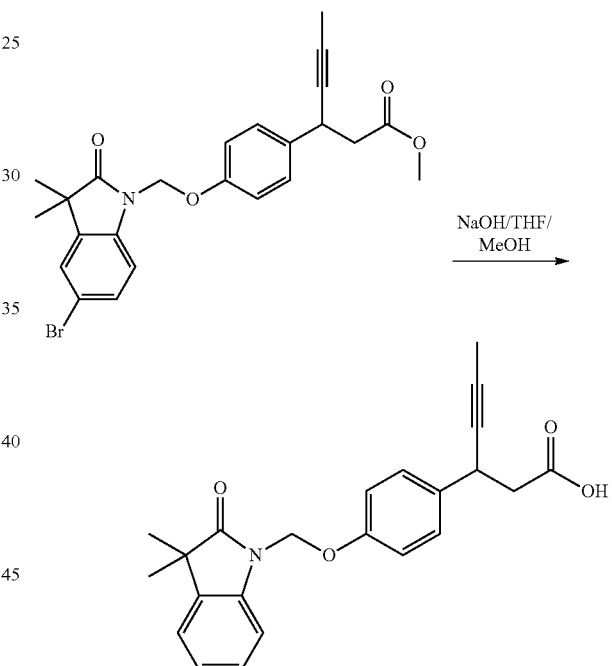

730 mg of methyl 3-[4-(5-bromo-3,3-dimethyl-2-oxo-2,3-dihydroindol-1-ylmethoxy)phenyl]-hex-4-ynoate were dissolved in a mixture of THF/MeOH/2N NaOH=1:1:1 (5 ml of each) and stirred at room temperature. After 1 hour, the mixture was acidified to pH 1 by addition of 2N HCl. 50 ml of water were added, the mixture was extracted three times with 50 ml each time of ethyl acetate. The combined organic phases were dried over MgSO$_4$, then concentrated under reduced pressure and purified on silica gel with the n-heptane/ethyl acetate solvent mixture as a linear gradient of 100% n-heptane=>100% ethyl acetate. This gave 620 mg of 3-[4-(5-bromo-3,3-dimethyl-2-oxo-2,3-dihydroindol-1-ylmethoxy)phenyl]-hex-4-ynoic acid.

$C_{23}H_{22}BrNO_4$ (456.34), LCMS (ESI-neg): 454.1, 456.1 (M−H$^+$).

Example 2

3-[4-(6-Bromo-3,3-dimethyl-2-oxo-2,3-dihydro-indol-1-ylmethoxy)phenyl]hex-4-ynoic acid

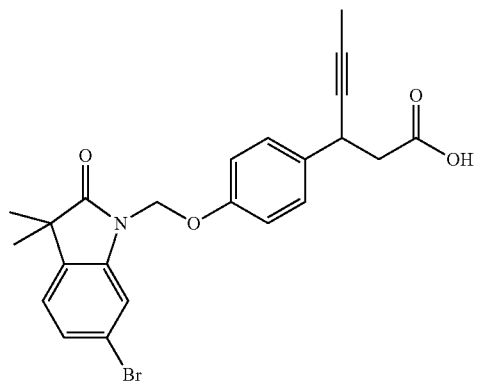 [SMILES: CC#CC(CC(=O)O)c1ccc(OCN2C(=O)C(C)(C)c3ccc(Br)cc32)cc1]

Analogously to example 1, 6-bromo-3,3-dimethyl-1,3-dihydroindol-2-one, chloromethyl pivalate and methyl 3-(4-hydroxyphenyl)hex-4-ynoate were used to obtain 3-[4-(6-bromo-3,3-dimethyl-2-oxo-2,3-dihydroindol-1-ylmethoxy)phenyl]hex-4-ynoic acid. $C_{23}H_{22}BrNO_4$ (456.34), LCMS (ESI-neg): 454.3, 456.1 (M−H$^+$).

Example 3

3-[4-(3,3-Dimethyl-2-oxo-5-trifluoromethyl-2,3-dihydroindol-1-ylmethoxy)phenyl]hex-4-ynoic acid

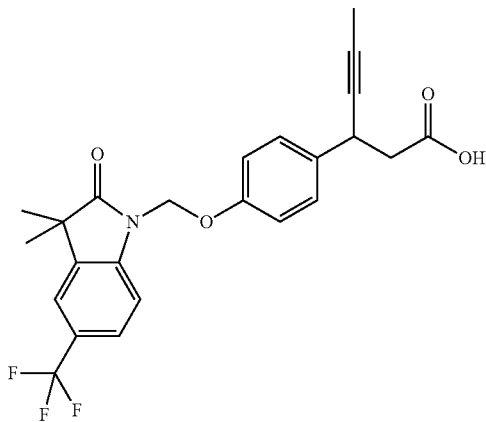 [SMILES: CC#CC(CC(=O)O)c1ccc(OCN2C(=O)C(C)(C)c3cc(C(F)(F)F)ccc32)cc1]

Analogously to example 1, 3,3-dimethyl-5-trifluoromethyl-1,3-dihydroindol-2-one, chloromethyl pivalate and methyl 3-(4-hydroxyphenyl)hex-4-ynoate were used to obtain 3-[4-(3,3-dimethyl-2-oxo-5-trifluoromethyl-2,3-dihydroindol-1-ylmethoxy)phenyl]hex-4-ynoic acid.

$C_{24}H_{22}F_3NO_4$ (445.44), LCMS (ESI-neg): 444.3 (M−H$^+$).

Example 4

3-[4-(7-Bromo-2,2-dimethyl-3-oxo-2,3-dihydrobenzo[1,4]oxazin-4-ylmethoxy)phenyl]hex-4-ynoic acid

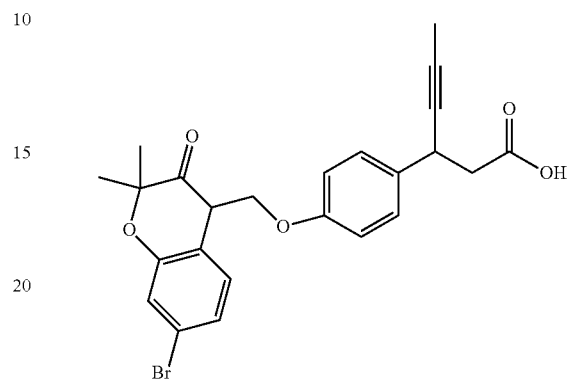

Analogously to example 1, 7-bromo-2,2-dimethyl-4H-benzo[1,4]oxazin-3-one, chloromethyl pivalate and methyl 3-(4-hydroxyphenyl)hex-4-ynoate were used to obtain 3-[4-(7-bromo-2,2-dimethyl-3-oxo-2,3-dihydrobenzo[1,4]oxazin-4-ylmethoxy)phenyl]hex-4-ynoic acid. $C_{23}H_{22}BrNO_5$ (472.34), LCMS (ESI-neg): 470.1, 472.1 (M−H$^+$).

Example 5

3-[4-(5-Bromo-3,3-diethyl-2-oxo-2,3-dihydroindol-1-ylmethoxy)phenyl]hex-4-ynoic acid

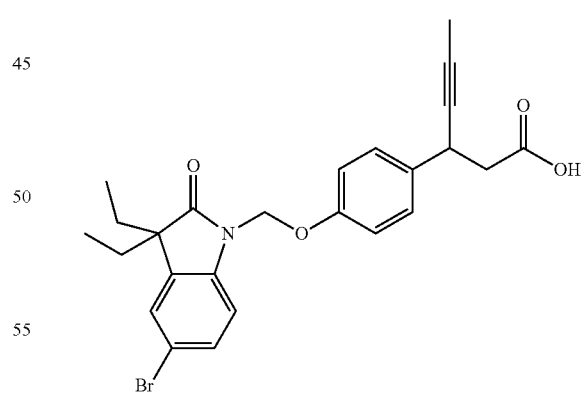

Analogously to example 1, 5-bromo-3,3-diethyl-1,3-dihydroindol-2-one, chloromethyl pivalate and methyl 3-(4-hydroxyphenyl)hex-4-ynoate were used to obtain 3-[4-(5-bromo-3,3-diethyl-2-oxo-2,3-dihydroindol-1-ylmethoxy)phenyl]hex-4-ynoic acid.

$C_{25}H_{26}BrNO_4$ (484.39), LCMS (ESI-neg): 482.3, 484.3 (M−H$^+$).

Example 6

3-[4-(6-Bromo-4,4-dimethyl-2-oxo-3,4-dihydro-2H-quinolin-1-ylmethoxy)phenyl]hex-4-ynoic acid

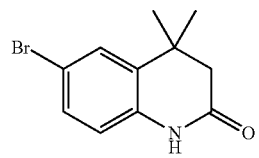

+

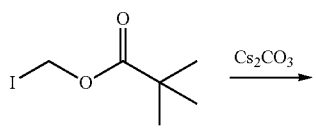 $\xrightarrow{Cs_2CO_3}$

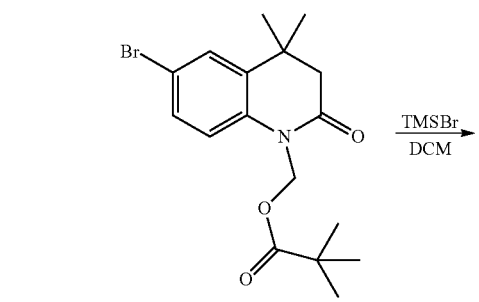 $\xrightarrow[DCM]{TMSBr}$

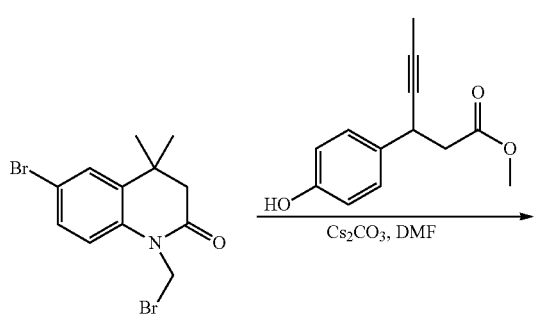 $\xrightarrow{Cs_2CO_3, DMF}$

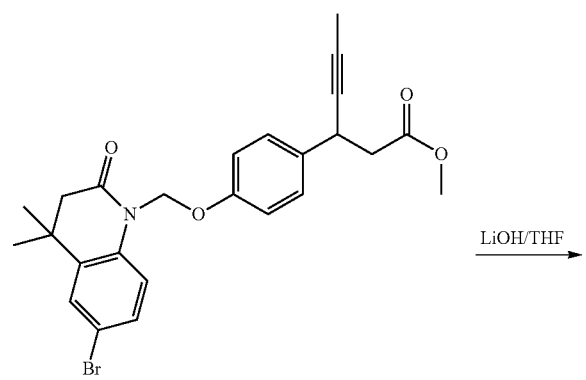 $\xrightarrow{LiOH/THF}$

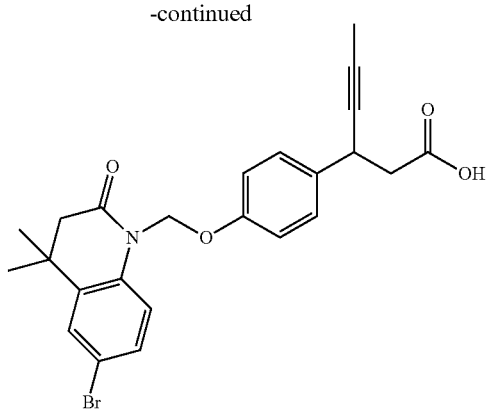

example 6

6-Bromo-4,4-dimethyl-2-oxo-3,4-dihydro-2H-quinolin-1-ylmethyl 2,2-dimethylpropionate

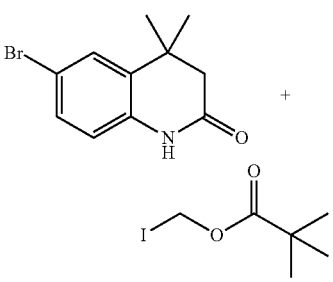 + 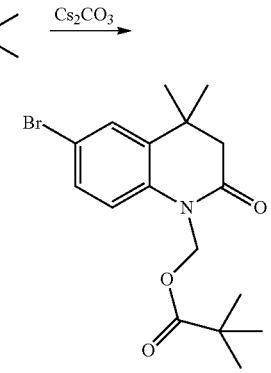 $\xrightarrow{Cs_2CO_3}$ 1.0 g of 6-bromo-3,4-dihydro-4,4-dimethylquinolin-2(1H)-one was dissolved in 10 ml of dry DMF, 3.85 g of cesium carbonate were added and 953 mg of iodomethyl pivalate were added dropwise while cooling with water, and the mixture was stirred at room temperature for 4 hours. The experiment was left to stand at room temperature overnight. Then a further 0.4 ml of iodomethyl pivalate was added at room temperature and the mixture was stirred at room temperature for a further 2 hours. (According to TLC and LC-MS, there is still reactant in the reaction solution). 50 ml of water were added, the mixture was extracted three times with 50 ml each time of ethyl acetate. The combined organic phases were dried over $MgSO_4$, then concentrated under reduced pressure and purified on silica gel with the n-heptane/ethyl acetate solvent mixture as a linear gradient of 100% n-heptane=>100% ethyl acetate. This gave 700 mg of 6-bromo-4,4-dimethyl-2-oxo-3,4-dihydro-2H-quinolin-1-ylmethyl 2,2-dimethylpropionate.

$C_{17}H_{22}BrNO_3$ (368.27), LCMS (ESI-pos): 266.0, 268.0 (M-pivalate⁻); TLC in n-heptane/ethyl acetate=4/1: $R_f$=0.29,

87

Methyl 3-[4-(6-bromo-4,4-dimeth-2-oxo-4-dihydro-2H-quinolin-1-ylmethoxy)phenyl]-hex-4-ynoate

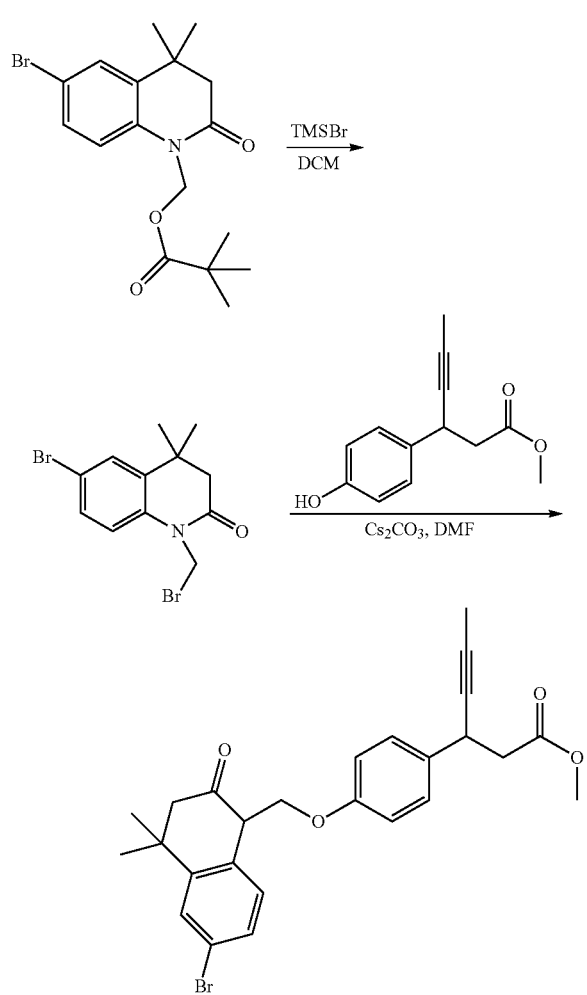

100 mg of 6-bromo-4,4-dimethyl-2-oxo-3,4-dihydro-2H-quinolin-1-ylmethyl 2,2-dimethylpropionate were dissolved in 2 ml of dichloromethane and cooled in an ice bath to 0° C. Then 71.7 μl of bromotrimethylsilane were slowly added dropwise. The mixture was stirred at 0° C. for 30 minutes while cooling with ice. Then the solvent was removed under reduced pressure. The residue was dissolved in 2 ml of dichloromethane and 5 ml of n-heptane. Then the solvents were removed once again under reduced pressure. The residue and 71 mg of methyl 3-(4-hydroxyphenyl)hex-4-ynoate were initially charged in 5 ml of dry DMF, 265 mg of cesium carbonate were added and the mixture was stirred at room temperature for 4 hours. The experiment was left to stand at room temperature overnight and was then diluted with 100 ml of ethyl acetate and extracted with 40 ml of water. The organic phase was removed and dried over MgSO$_4$, filtered and then concentrated under reduced pressure. The residue was purified on silica gel with the n-heptane/ethyl acetate solvent mixture=4:1. This gave 91 mg of methyl 3-[4-(6-bromo-4,4-dimethyl-2-oxo-3,4-dihydro-2H-quinolin-1-ylmethoxy)phenyl]hex-4-ynoate.

$C_{25}H_{26}BrNO_4$ (484.39), LCMS (ESI-pos): 484.1, 486.1 (M+H$^+$); TLC in n-heptane/ethyl acetate=4:1: R$_f$=0.15.

88

3-[4-(6-Bromo-4,4-dimethyl-2-oxo-3,4-dihydro-2H-quinolin-1-ylmethoxy)phenyl]hex-4-ynoic acid

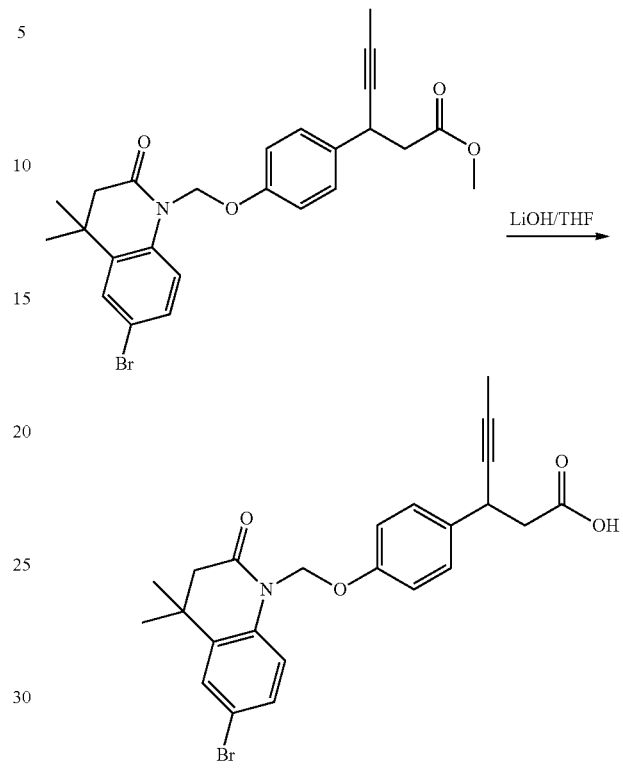

example 6

91 mg of methyl 3-[4-(6-bromo-4,4-dimethyl-2-oxo-3,4-dihydro-2H-quinolin-1-ylmethoxy)-phenyl]hex-4-ynoate were dissolved in 1.4 ml of tetrahydrofuran, and 1N LiOH solution was added. The experiment was stirred at room temperature for 2 hours and left to stand at room temperature overnight. Subsequently, 2N H$_2$SO$_4$ was used to adjust the pH to 1 and the mixture was extracted with 80 ml of ethyl acetate. The organic phase was removed and dried over MgSO$_4$, filtered and then concentrated under reduced pressure. The residue was purified by means of RP-HPLC. This gave 27.0 mg of 3-[4-(6-bromo-4,4-dimethyl-2-oxo-3,4-dihydro-2H-quinolin-1-ylmethoxy)phenyl]hex-4-ynoic acid, $C_{24}H_{24}BrNO_4$ (470.37), LCMS (ESI-neg): 468.3, 470.3 (M−H$^+$).

Example 7

3-[4-(2-Oxobenzothiazol-3-ylmethoxy)phenyl]hex-4-ynoic acid

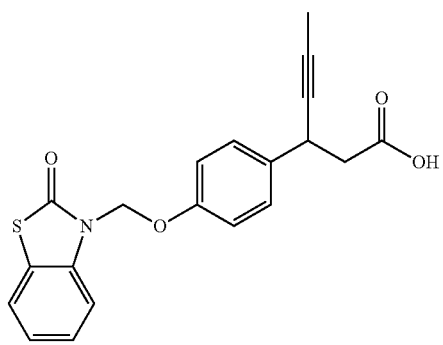 [SMILES: CC#CC(CC(=O)O)c1ccc(OCn2c(=O)sc3ccccc32)cc1]

Analogously to example 6, 3H-benzothiazol-2-one, iodomethyl pivalate and methyl 3-(4-hydroxyphenyl)hex-4-ynoate were used to obtain 3-[4-(2-oxobenzothiazol-3-yl-methoxy)-phenyl]hex-4-ynoic acid.

$C_{20}H_{17}NO_4S$ (367.43), LCMS (ESI-neg): 366.3 (M−H$^+$).

Example 8

3-[4-(2,2-Dimethyl-3-oxo-2,3-dihydrobenzo[1,4]oxazin-4-ylmethoxy)phenyl]hex-4-ynoic acid

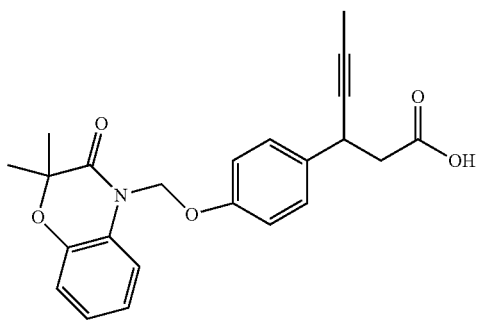 [SMILES: CC#CC(CC(=O)O)c1ccc(OCN2C(=O)C(C)(C)Oc3ccccc32)cc1]

Analogously to example 6, 2,2-dimethyl-4H-benzo[1,4]oxazin-3-one, iodomethyl pivalate and methyl 3-(4-hydroxyphenyl)hex-4-ynoate were used to obtain 3-[4-(2,2-dimethyl-3-oxo-2,3-dihydrobenzo[1,4]oxazin-4-ylmethoxy)phenyl]hex-4-ynoic acid.

$C_{23}H_{23}NO_5$ (393.44), LCMS (ESI-pos): 394.2 (M+H$^+$).

Example 9

3-[4-(2,2-Dimethyl-3-oxo-2,3-dihydrobenzo[1,4]oxazin-4-ylmethoxy)phenyl]hex-4-ynoic acid

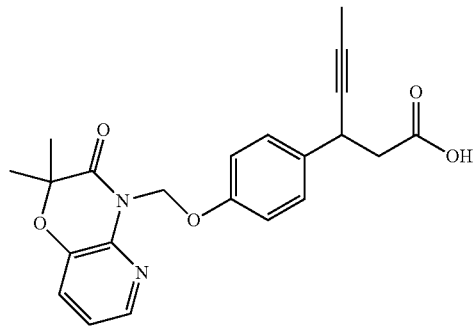 [SMILES: CC#CC(CC(=O)O)c1ccc(OCN2C(=O)C(C)(C)Oc3cccnc32)cc1]

Analogously to example 6, 2,2-dimethyl-4H-pyrido[3,2-b][1,4]oxazin-3-one, iodomethyl pivalate and methyl 3-(4-hydroxyphenyl)hex-4-ynoate were used to obtain 3-[4-(2,2-dimethyl-3-oxo-2,3-dihydrobenzo[1,4]oxazin-4-ylmethoxy)phenyl]hex-4-ynoic acid.

$C_{22}H_{22}N_2O_5$ (394.43), LCMS (ESI-pos): 395.3 (M+H$^+$).

Example 10

3-[4-(2,2,6-Trimethyl-3-oxo-2,3-dihydrobenzo[1,4]oxazin-4-ylmethoxy)phenyl]hex-4-ynoic acid

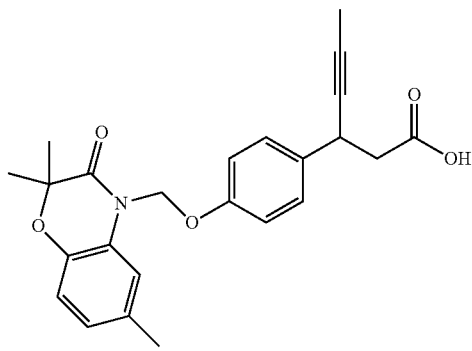 [SMILES: CC#CC(CC(=O)O)c1ccc(OCN2C(=O)C(C)(C)Oc3ccc(C)cc32)cc1]

Analogously to example 6, 2,2,6-trimethyl-4H-benzo[1,4]oxazin-3-one, iodomethyl pivalate and methyl 3-(4-hydroxyphenyl)hex-4-ynoate were used to obtain 3-[4-(2,2,6-trimethyl-3-oxo-2,3-dihydrobenzo[1,4]oxazin-4-ylmethoxy)phenyl]hex-4-ynoic acid.

$C_{24}H_{25}NO_5$ (407.47), LCMS (ESI-neg): 406.4 (M−H$^+$).

The invention claimed is:
1. A compound of formula I

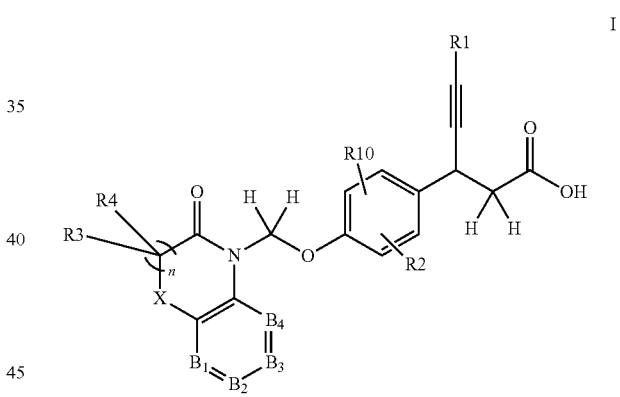

wherein
R1 is H, ($C_1$-$C_6$)-alkyl, ($C_3$-$C_6$)-cycloalkyl, or ($C_1$-$C_6$)-alkylene-($C_3$-$C_{10}$)-cycloalkyl, where the alkyl radical, alkylene radical or cycloalkyl radical may be mono- or polysubstituted by fluorine;
R2, and R10 are each independently H, F, Cl, Br, CN, ($C_1$-$C_6$)-alkyl, or O—($C_1$-$C_6$)-alkyl, where the alkyl radical may be mono- or polysubstituted by fluorine;
X is a bond, —O—, —S—, —SO—, —SO$_2$—, —CO—, —(CR7R8)-, —CH$_2$—CH$_2$—, —CH$_2$O—, —OCH$_2$—, —CH$_2$S—, —SCH$_2$—, —CH$_2$SO—, —SOCH$_2$—, —CH$_2$SO$_2$—, —SO$_2$CH$_2$—, or —N(R11)-;
B$_1$, B$_2$, B$_3$, and B$_4$ are each independently —N— or —C(R9)-;
R3, R4, R7, and R8 are each independently H, ($C_1$-$C_6$)-alkyl, ($C_3$-$C_{10}$)-cycloalkyl, or ($C_1$-$C_6$)-alkylene-($C_3$-$C_{10}$)-cycloalkyl, where the alkyl radical, alkylene radical or cycloalkyl radical may be mono- or polysubstituted by fluorine;

R9 is H, F, Cl, Br, I, OH, $NO_2$, CN, O—$(C_1$-$C_6)$-alkyl, $(C_1$-$C_6)$-alkyl, $SO_2$—$CH_3$, $SO_2$—$NH_2$, $SO_2$—$NH(C_1$-$C_6)$-alkyl, $SO_2$—$N((C_1$-$C_6)$-alkyl$)_2$, $CONH_2$, CONH $(C_1$-$C_6)$-alkyl, $CON((C_1$-$C_6)$-alkyl$)_2$, $SF_5$, $(C_6$-$C_{10})$-aryl, $(C_3$-$C_{10})$-cycloalkyl, or a 4- to 12-membered heterocycle, where the $(C_1$-$C_6)$-alkyl radical, $(C_6$-$C_{10})$-aryl radical, $(C_3$-$C_{10})$-cycloalkyl radical, or 4- to 12-membered heterocycle radical may be mono- or polysubstituted by F, Cl, Br, I, OH, $CF_3$, O—$(C_1$-$C_6)$-alkyl, $(C_1$-$C_6)$-alkyl, or $SF_5$;

R11 is H, $(C_1$-$C_6)$-alkyl, or —CO—$(C_1$-$C_6)$-alkyl; and n is 0, 1, or 2;

or a physiologically compatible salt thereof.

2. The compound as claimed in claim 1, wherein

R1 is H, $(C_1$-$C_6)$-alkyl, $(C_3$-$C_6)$-cycloalkyl, or $(C_1$-$C_6)$-alkylene-$(C_3$-$C_{10})$-cycloalkyl, where the alkyl radical, alkylene radical or cycloalkyl radical may be mono- or polysubstituted by fluorine;

R2, and R10 are each independently H, F, Cl, Br, CN, $(C_1$-$C_6)$-alkyl, or O—$(C_1$-$C_6)$-alkyl, where the alkyl radical may be mono- or polysubstituted by fluorine;

X is a bond, —O—, —S—, or —(CR7R8)-;

$B_1$, $B_2$, $B_3$, and $B_4$ are each independently —N— or —C(R9)-;

R3, R4, R7, and R8 are each independently H, $(C_1$-$C_6)$-alkyl, $(C_3$-$C_{10})$-cycloalkyl, or $(C_1$-$C_6)$-alkylene-$(C_3$-$C_{10})$-cycloalkyl, where the alkyl radical, alkylene radical and cycloalkyl radical may be mono- or polysubstituted by fluorine;

R9 is H, F, Cl, Br, I, OH, $NO_2$, CN, O—$(C_1$-$C_6)$-alkyl, $(C_1$-$C_6)$-alkyl, $SO_2$—$CH_3$, $SO_2$—$NH_2$, $SO_2$—$NH(C_1$-$C_6)$-alkyl, $SO_2$—$N((C_1$-$C_6)$-alkyl$)_2$, $CONH_2$, CONH $(C_1$-$C_6)$-alkyl, $CON((C_1$-$C_6)$-alkyl$)_2$, $SF_5$, $(C_6$-$C_{10})$-aryl, $(C_3$-$C_{10})$-cycloalkyl, or a 4- to 12-membered heterocycle, where the $(C_1$-$C_6)$-alkyl radical, $(C_6$-$C_{10})$-aryl radical, $(C_3$-$C_{10})$-cycloalkyl radical, or 4- to 12-membered heterocycle radical may be mono- or polysubstituted by F, Cl, Br, I, OH, $CF_3$, O—$(C_1$-$C_6)$-alkyl, $(C_1$-$C_6)$-alkyl, or $SF_5$; and n is 0 or 1;

or a physiologically compatible salt thereof.

3. The compound as claimed in claim 1, wherein

R1 is $(C_1$-$C_6)$-alkyl, where the alkyl radical may be mono- or polysubstituted by fluorine;

R2 is H, F, Cl, Br, CN, $(C_1$-$C_6)$-alkyl, or O—$(C_1$-$C_6)$-alkyl, where the alkyl radical may be mono- or polysubstituted by fluorine;

R10 is H;

X is a bond, —O—, —S—, —(CR7R8)-;

$B_1$, $B_2$, $B_3$, and $B_4$ are each independently —N— or —C(R9)-;

R3 and R4 are each independently H or $(C_1$-$C_6)$-alkyl;

R7 and R8 are each independently H or $(C_1$-$C_6)$-alkyl;

R9 is H, F, Cl, Br, OH, $(C_1$-$C_6)$-alkyl, where the $(C_1$-$C_6)$-alkyl radical may be mono- to trisubstituted by F; and n is 0 or 1;

or a physiologically compatible salt thereof.

4. The compound as claimed in claim 1, wherein

R1 is $(C_1$-$C_6)$-alkyl, where the alkyl radical may be mono- or polysubstituted by fluorine;

R2 is H, F, Cl, Br, CN, $(C_1$-$C_6)$-alkyl, or O—$(C_1$-$C_6)$-alkyl, where the alkyl radical may be mono- or polysubstituted by fluorine;

R10 is H;

X is a bond, —O—, —S—, or —(CR7R8)-;

$B_1$, $B_2$, $B_3$, and $B_4$ are each independently —N— or —C(R9)-;

R3 and R4 are each independently H or $(C_1$-$C_6)$-alkyl;

R7 and R8 are each independently H or $(C_1$-$C_6)$-alkyl;

R9 is H, F, Cl, Br, OH, or $(C_1$-$C_6)$-alkyl, where the $(C_1$-$C_6)$-alkyl radical may be mono- to trisubstituted by F; and n is 0 or 1;

or a physiologically compatible salt thereof.

5. A pharmaceutical composition comprising one or more compounds as claimed in claim 1.

6. The pharmaceutical composition as claimed in claim 5, which comprises at least one further active ingredient.

7. The pharmaceutical composition as claimed in claim 6, which comprises, as a further active ingredient, one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase modulators, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine: fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART modulators, NPY agonists, MC4 agonists, orexin receptor 1 antagonists, orexin receptor 2 antagonists, H3 agonists, TNF agonists, CRF antagonists, CRF BP antagonists, urocortin agonists, β3 agonists, CB1 receptor antagonists, MSH (melanocyte-stimulating hormone) agonists, CCK-A modulators, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists, lipase/amylase inhibitors, PPAR modulators, RXR modulators or TR-β-agonists or amphetamines.

8. The pharmaceutical composition as claimed in claim 6, which comprises, as a further active ingredient, metformin, arcabose, glibenclamide, glimepiride, gliclazide, gliquidone, pioglitazone, rosiglitazone, exenatide, miglitol, vildagliptin, sitagliptin, repaglinide, nateglinide or mitiglinide.

9. A method for lowering blood glucose in a patient in need thereof comprising administering to said patient a therapeutically effective amount of the pharmaceutical composition of claim 5.

10. A method for treating diabetes in a patient in need thereof comprising administering to said patient a therapeutically effective amount of the pharmaceutical composition of claim 5.

11. A method for increasing insulin excretion in a patient in need thereof comprising administering to said patient a therapeutically effective amount of the pharmaceutical composition of claim 5.

12. A process for preparing the pharmaceutical composition as claimed in claim 5, comprising mixing the active ingredient with a pharmaceutically suitable carrier to form a mixture suitable for administration.

* * * * *